United States Patent
Li et al.

(10) Patent No.: US 7,372,071 B2
(45) Date of Patent: *May 13, 2008

(54) FUNCTIONALIZED HETEROACENES AND ELECTRONIC DEVICES GENERATED THEREFROM

(75) Inventors: Yuning Li, Mississauga (CA); Yiliang Wu, Mississauga (CA); Beng S. Ong, Mississauga (CA); Ping Liu, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/398,981

(22) Filed: Apr. 6, 2006

(65) Prior Publication Data

US 2007/0235721 A1    Oct. 11, 2007

(51) Int. Cl.
H01L 51/00 (2006.01)
H01L 29/08 (2006.01)
H01L 35/24 (2006.01)
(52) U.S. Cl. .................. 257/40; 257/E51.029
(58) Field of Classification Search .................. 257/40
See application file for complete search history.

(56) References Cited

U.S. PATENT DOCUMENTS 5,619,357 A    4/1997    Angelopoulos et al.

(Continued)

FOREIGN PATENT DOCUMENTS

| JP | 10-340786 | * 12/1998 |
| JP | 2005-206750 | * 8/2005 |

OTHER PUBLICATIONS

Kuo et al., "TES Anthradithiophene Solution-Processed OTFTs with 1 cm2/V-s Mobility," Technical Digest—International Electron Devices Meeting (2004), pp. 373-376.*

(Continued)

*Primary Examiner*—Jerome Jackson
*Assistant Examiner*—Anthony Ho
(74) *Attorney, Agent, or Firm*—Eugene O. Palazzo; Fay Sharpe LLP

(57) ABSTRACT

An electronic device, such as a thin film transistor containing a semiconductor of, for example, of the Formula (I)

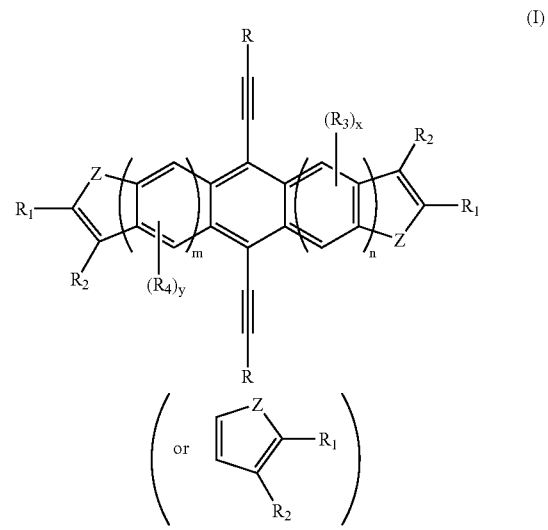

wherein R represents alkyl, alkoxy, aryl, heteroaryl or a suitable hydrocarbon; each $R_1$ and $R_2$ is independently hydrogen (H), a suitable hydrocarbon; a heteroatom containing group or a halogen; $R_3$ and $R_4$ are independently a suitable hydrocarbon, a heteroatom containing group, or a halogen; x and y represent the number of groups; Z represents sulfur, oxygen, selenium, or NR' wherein R' is hydrogen, alkyl, or aryl; and n and m represent the number of repeating units.

34 Claims, 2 Drawing Sheets

U.S. PATENT DOCUMENTS

| | | | |
|---|---|---|---|
| 5,777,070 | A | 7/1998 | Inbasekaran et al. |
| 5,936,259 | A * | 8/1999 | Katz et al. .................... 257/40 |
| 5,969,376 | A | 10/1999 | Bao |
| 6,107,117 | A | 8/2000 | Bao et al. |
| 6,150,191 | A | 11/2000 | Bao |
| 6,690,029 | B1 * | 2/2004 | Anthony et al. .............. 257/40 |
| 6,770,904 | B2 | 8/2004 | Ong et al. |
| 2003/0102471 | A1 * | 6/2003 | Kelley et al. ................. 257/40 |
| 2003/0209692 | A1 * | 11/2003 | Farrand et al. ........ 252/299.61 |
| 2005/0017311 | A1 | 1/2005 | Ong et al. |
| 2007/0102696 | A1 * | 5/2007 | Brown et al. ................. 257/40 |

OTHER PUBLICATIONS

Payne et al., "Organic Field-Effect Transistors from Solution-Deposited Functionalized Acenes with Mobilities as High as 1 cm2/V-s," Journal of the American Chemical Society (2005), 127(14), pp. 4986-4987.*

Payne et al, "Stable, Crystalline Acenedithiophenes with up to Seven Linearly Fused Rings", Organic Letters, 2004, vol. 6, No. 19, pp. 3325-3328.*

See the "Cross Reference to Related Applications" on pp. 1 and 2 of the Specification Being Filed Concurrently.

Ong, Beng, et al., U.S. Appl. No. 11/011,678, filed Dec. 14, 2004 on Compound with Indolocarbazole Moieties and Devices Containing Such Compound.

Ong, Beng, et al., U.S. Appl. No. 11/167,512, filed Jun. 27, 2005 on Compound with Indolocarbazole Moieties and Devices Containing Such Compound.

Huang, D.H., et al., "Conjugated Polymers Based on Phenothiazine and Fluorene in Light-Emitting Diodes and Field Effect Transistors", *Chem. Mater. 2004*, 16, 1298-1303.

Zhu, Y., et al, "Phenoxazine-Based Conjugated Polymers: A New Class of Organic Semiconductors for Field-Effect Transistors", *Macromolecules 2005*, 38, 7983-7991.

* cited by examiner

FUNCTIONALIZED HETEROACENES AND ELECTRONIC DEVICES GENERATED THEREFROM

STATEMENT REGARDING FEDERALLY SPONSORED RESEARCH OR DEVELOPMENT

The electronic devices and certain components thereof were supported by a United States Government Cooperative Agreement No. 70NANBOH3033 awarded by the National Institute of Standards and Technology (NIST). The United States Government has certain rights relating to the devices and certain semiconductor components illustrated hereinafter.

CROSS REFERENCE TO RELATED APPLICATIONS

U.S. application Ser. No. 11/399,226, filed concurrently herewith, on Functionalized Heteroacenes, by Yuning Li et al.

U.S. application Ser. No. 11/399,216, filed concurrently herewith, on Polyacenes and Electronic Devices Generated Therefrom, by Yuning Li et al.

U.S. application Ser. No. 11/399,064, filed concurrently herewith, on Heteroacene Polymers and Electronic Devices Generated Therefrom, by Yuning Li et al.

U.S. application Ser. No. 11/399,169, filed concurrently herewith, on Ethynylene Acene Polymers and Electronic Devices Generated Therefrom, by Yuning Li et al.

U.S. application Ser. No. 11/399,091, filed concurrently herewith, on Ethynylene Acene Polymers, by Yuning Li et al.

U.S. application Ser. No. 11/399,231, filed concurrently herewith, on Poly[bis(ethynyl)heteroacenes] and Electronic Devices Generated Therefrom, by Yuning Li et al.

U.S. application Ser. No. 11/399,141, filed concurrently herewith, on Semiconductors and Electronic Devices Generated Therefrom, by Yiliang Wu et al.

U.S. application Ser. No. 11/399,230, filed concurrently herewith, on Semiconductor Polymers, by Yiliang Wu et al.

U.S. application Ser. No. 11/399,941, filed concurrently herewith, on Polydiazaacenes and Electronic Devices Generated Therefrom, by Yiliang Wu et al.

U.S. application Ser. No. 11/399,092, filed concurrently herewith, on Polydiazaacenes, by Yiliang Wu et al.

U.S. application Ser. No. 11/398,931, filed concurrently herewith, on Poly(alkynylthiophene)s and Electronic Devices Generated Therefrom, by Beng S. Ong et al.

U.S. application Ser. No. 11/399,246, filed concurrently herewith, on Poly(alkynylthiophene)s, by Beng S. Ong et al.

U.S. application Ser. No. 11/399,092, filed concurrently herewith, on Linked Arylamine Polymers and Electronic Devices Generated Therefrom, by Yuning Li et al.

U.S. application Ser. No. 11/399,065, filed concurrently herewith, on Linked Arylamine Polymers, by Yuning Li et al.

Illustrated in U.S. application Ser. No. 11/011,678 filed Dec. 14, 2004, now abandoned, relating to indolocarbazole moieties and thin film transistor devices thereof.

Illustrated in U.S. application Ser. No. 11/167,512 filed Jun. 27, 2005, U.S. Publication 20060214155, relating to indolocarbazole moieties and thin film transistor devices thereof.

Illustrated in U.S. Pat. No. 6,770,904 and copending application U.S. application Ser. No. 10/922,662, Publication No. 20050017311, are electronic devices, such as thin film transistors containing semiconductor layers of, for example, polythiophenes.

The disclosure of each of the above cross referenced applications and patent is totally incorporated herein by reference. In aspects of the present disclosure, there may be selected the appropriate substituents, such as a suitable hydrocarbon, a heteroatom containing group, hydrogen, halogen, CN, $NO_2$, rings, number of repeating polymer units, number of groups, and the like as illustrated in the copending applications.

The appropriate components, processes thereof and uses thereof illustrated in these copending applications and patents may be selected for the present invention in embodiments thereof.

BACKGROUND

The present disclosure is generally directed to polymers and uses thereof. More specifically, the present disclosure in embodiments is directed to a class of heteroacenes functionalized with, for example, alkylethynyl or alkylarylethynyl groups, and other suitable groups as illustrated herein, and which components can be selected as solution processable and substantially stable channel semiconductors in organic electronic devices, such as thin film transistors.

There are desired electronic devices, such as thin film transistors, TFTs, fabricated with the polymers illustrated herein, such as functionalized heteroacenes with excellent solvent solubility, which can be solution processable; and devices with mechanical durability and structural flexibility, which may be highly desirable for fabricating flexible TFTs on plastic substrates. Flexible TFTs would enable the design of electronic devices which usually involve structural flexibility and mechanical durability characteristics. The use of plastic substrates together with the functionalized heteroacene components can transform the traditionally rigid silicon TFT into a mechanically more durable and structurally flexible TFT design. This is of particular value to large area devices, such as large-area image sensors, electronic paper and other display media. Also, the selection of functionalized heteroacenes TFTs for integrated circuit logic elements for low end microelectronics, such as smart cards, radio frequency identification (RFID) tags, and memory/storage devices, may enhance their mechanical durability, and thus their useful life span.

A number of semiconductor materials are not, it is believed, stable when exposed to air as they become oxidatively doped by ambient oxygen, resulting in increased conductivity. The result is a large off-current and thus a low current on/off ratio for the devices fabricated from these materials. Accordingly, with many of these materials, rigorous precautions are usually undertaken during materials processing and device fabrication to exclude environmental oxygen to avoid or minimize oxidative doping. These precautionary measures increase the cost of manufacturing therefore offsetting the appeal of certain semiconductor TFTs as an economical alternative to amorphous silicon technology, particularly for large area devices. These and other disadvantages are avoided or minimized in embodiments of the present disclosure.

REFERENCES

Heteroacenes are known to possess acceptable high field effect mobility when used as channel semiconductors in TFTs. However, these materials are rapidly oxidized by, for example, atmospheric oxygen under light, and such materials are not considered processable at ambient conditions. Furthermore, heteroacenes, when selected for TFTs, have poor thin film formation characteristics, and are substantially insoluble or have minimal solubility in a number of commonly used solvents rendering these compounds as being nonsolution processing; accordingly, such compounds have been mostly processed by vacuum deposition methods that result in high production costs, and which disadvantages are eliminated or minimized with the TFTs generated with the functionalized heterocenes illustrated herein.

A number of organic semiconductor materials has been described for use in field effect TFTs, which materials include organic small molecules such as pentacene, see for example D. J. Gundlach et al., "Pentacene organic thin film transistors—molecular ordering and mobility", *IEEE Electron Device Lett.*, Vol. 18, p. 87 (1997); oligomers, such as sexithiophenes or their variants, see for example reference F. Gamier et al., "Molecular engineering of organic semiconductors: Design of self-assembly properties in conjugated thiophene oligomers", *J. Amer. Chem. Soc.*, Vol. 115, p. 8716 (1993), and certain functionalized heteroacenes, such as poly(3-alkylthiophene), see for example reference Z. Bao et al., "Soluble and processable regioregular poly(3-hexylthiophene) for field-effect thin film transistor application with high mobility", *Appl. Phys. Lett.* Vol. 69, p 4108 (1996). Although organic material based TFTs generally provide lower performance characteristics than their conventional silicon counterparts, such as silicon crystal or polysilicon TFTs, they may nonetheless be sufficiently useful for applications in areas where high mobility is not required. These devices may include large area devices, such as image sensors, active matrix liquid crystal displays and low end microelectronics, such as smart cards and RFID tags.

TFTs fabricated from the polymers illustrated herein, such as functionalized heteroacenes, may be functionally and structurally more desirable than conventional silicon technology in that they may offer mechanical durability, while also avoiding vacuum deposition, structural flexibility, and the potential of being able to be incorporated directly onto the active media of the devices thus enhancing device compactness for transportability.

With vacuum deposition, it is difficult to achieve consistent thin film quality for large area formats. Polymer TFTs, such as those fabricated from regioregular components, of, for example, regioregular poly(3-alkylthiophene-2,5-diyl) by solution processes, while offering some mobility, suffer from their propensity toward oxidative doping in air. For practical low cost TFT design, it is therefore of value to have a semiconductor material that is both stable and solution processable, and where its performance is not adversely affected by ambient oxygen, for example, TFTs generated with poly(3-alkylthiophene-2,5-diyl) are very sensitive to air. The TFTs fabricated from these materials in ambient conditions generally exhibit very large off-current, very low current on/off ratios, and their performance characteristics degrade rapidly.

Illustrated in Huang, D. H., et al, *Chem. Mater.* 2004, 16, 1298-1303, are, for example, LEDS and field effect transistors based on certain phenothiaazines like poly(10-(2-ethylhexyl)phenothiaazine).

Illustrated in Zhu, Y., et al, *Macromolecules* 2005, 38, 7983-7991, are, for example semiconductors based on phenoxazine conjugated polymers like poly(10-hexylphenoxazine).

Additional references that may be of interest include U.S. Pat. Nos. 6,150,191; 6,107,117; 5,969,376; 5,619,357, and 5,777,070, the disclosures of which are totally incorporated herein by reference.

BRIEF DESCRIPTION OF THE DRAWINGS

Illustrated in FIGS. 1 to 4 are various representative embodiments of the present disclosure, and wherein polymers like functionalized heteroacenes are selected as the channel or semiconductor material in thin film transistor (TFT) configurations.

DESCRIPTION OF THE EXEMPLARY EMBODIMENTS

Figure 1:
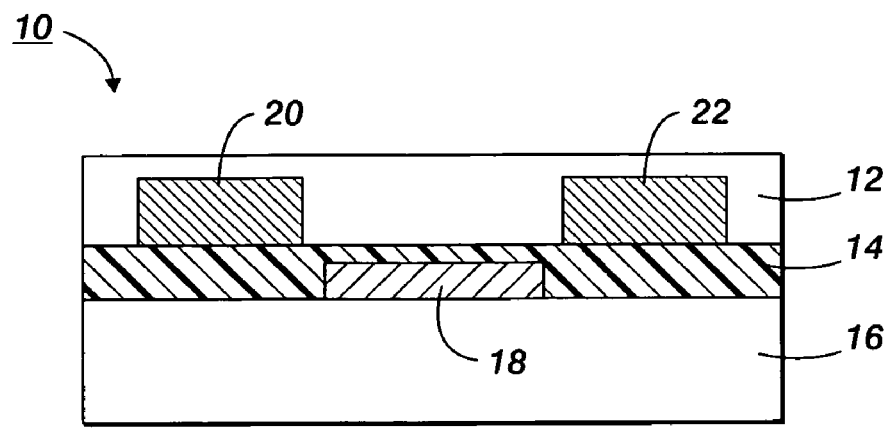

It is a feature of the present disclosure to provide polymer semiconductors, which are useful in microelectronic device applications, such as TFT devices.

It is another feature of the present disclosure to provide functionalized heteroacenes with a band gap of from about 1.5 eV to about 3 eV as determined from the absorption spectra of thin films thereof, and which functionalized heteroacenes are suitable for use as TFT semiconductor channel layer materials.

In yet a further feature of the present disclosure there are provided functionalized heteroacenes which are useful as microelectronic components, and which functionalized heteroacenes possess solubility of, for example, at least about 0.1 percent to about 95 percent by weight in common organic solvents, such as methylene chloride, tetrahydrofuran, toluene, xylene, mesitylene, chlorobenzene, and the like, and thus these components can be economically fabricated by solution processes such as spin coating, screen printing, stamp printing, dip coating, solution casting, jet printing, and the like.

Another feature of the present disclosure resides in providing electronic devices, such as TFTs, with a functionalized heteroacene channel layer, and which layer has a conductivity of from about $10^{-4}$ to about $10^{-9}$ S/cm (Siemens/centimeter).

Also, in yet another feature of the present disclosure there are provided novel polymers like functionalized heteroacenes and devices thereof, and which devices exhibit enhanced resistance to the adverse effects of oxygen, that is, these devices exhibit relatively high current on/off ratios, and their performance does not substantially degrade as rapidly as similar devices fabricated with regioregular poly(3-alkylthiophene-3,5-diyl) or with heteroacenes.

Additionally, in a further feature of the present disclosure there is provided a class of novel polymers like functionalized heteroacenes with unique structural features, which are conducive to molecular self-alignment under appropriate processing conditions, and which structural features also enhance the stability of device performance. Proper molecular alignment can permit higher molecular structural order in thin films, which can be important to efficient charge carrier transport, thus higher electrical performance.

There are disclosed in the embodiments, polymers like functionalized heteroacenes and electronic devices thereof. More specifically, the present disclosure relates to polymers illustrated by or encompassed by Formula (I)

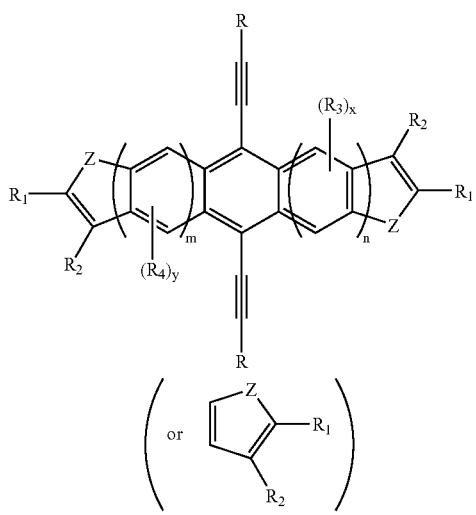

(I)

wherein R represents a suitable hydrocarbon like alkyl, aryl, or heteroaryl; each $R_1$ and $R_2$ is independently hydrogen (H), a suitable hydrocarbon; a heteroatom containing group or a halogen; $R_3$ and $R_4$ are independently a suitable hydrocarbon, a heteroatom containing group, or a halogen; x and y represent the number of groups; Z represents sulfur, oxygen, selenium, or NR' wherein R' is hydrogen, alkyl, or aryl; m and n each represent the number of rings, such as for example from zero (0) to about 3; and more specifically, x and y can be, for example, from zero to about 12, and more specifically, wherein each x and y are from about 3 to about 7.

Examples of alkyl with, for example, from about 1 to about 30, including from about 4 to about 18 carbon atoms (included throughout are numbers within the range, for example 4, 5, 6, 7, 8, 9, 10, 11, 12, 13, 14, 15, 16, 17 and 18), and further including from about 6 to about 16 carbon atoms are butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, or eicosanyl, isomeric forms thereof, mixtures thereof, and the like; alkylaryl with from about 7 to about 49 carbon atoms, from about 6 to about 37 carbon atoms, from about 13 to about 25 carbon atoms, such as methyl phenyl, substituted phenyls, and the like; or aryl, such as phenyl with about 6 to about 48 carbon atoms.

Heteroatom containing groups include, for example, polyethers, trialkylsilyls, heteroaryls, and the like; and more specifically, thienyl, furyl and pyridiaryl. The hetero component can be selected from a number of known atoms like sulfur, oxygen, nitrogen, silicon, selenium, and the like.

In embodiments, R can be an unbranched alkyl of, for example, from about 2 to about 16 carbon atoms; an unbranched alkylaryl where alkyl contains, for example, from about 4 to about 12 carbon atoms; $R_1$ and $R_{12}$ are hydrogen, alkyl, aryl, halogen, cyano, nitro, and the like; m and n are each zero, or from 1 to about 3; and x and y are each zero, or from 1 to about 12.

Hydrocarbons are known and include alkyl, alkoxy, aryl, alkylaryl, substituted alkyl, alkoxy, aryl, and the like. Specific illustrative examples are (1)

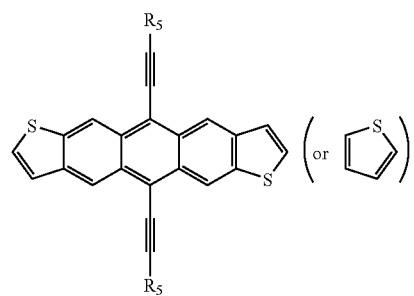

(2)

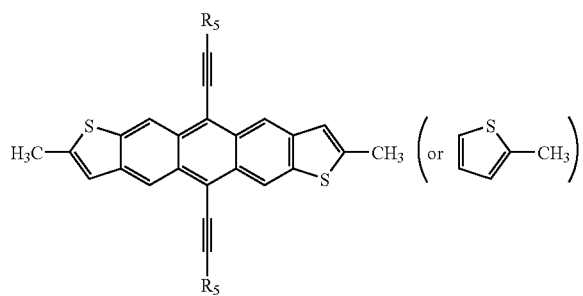

(3)

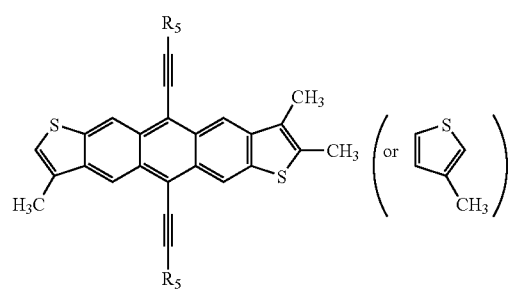

(4)

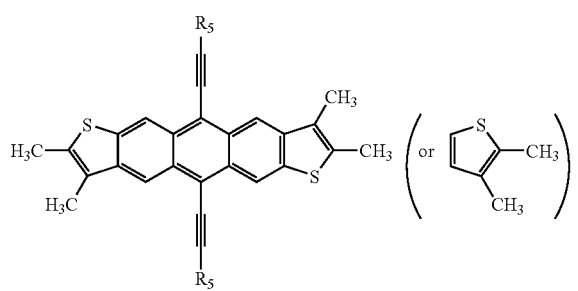

-continued
(5)
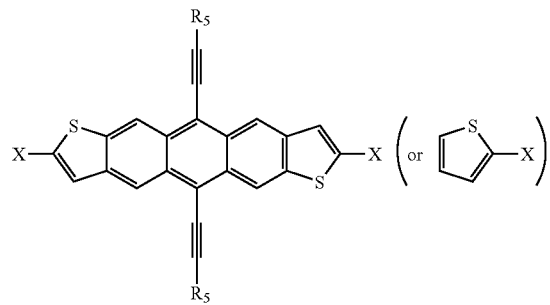
(6)
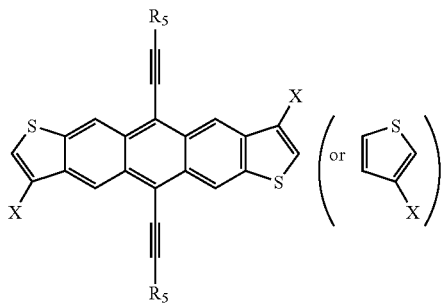
(7)
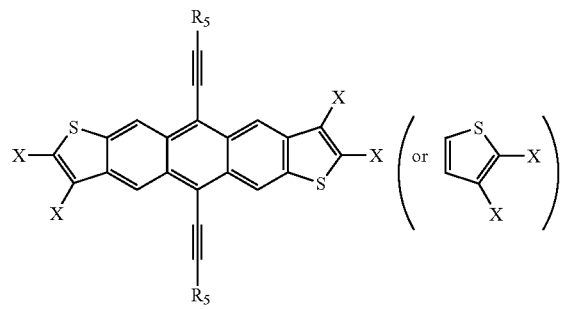
(8)
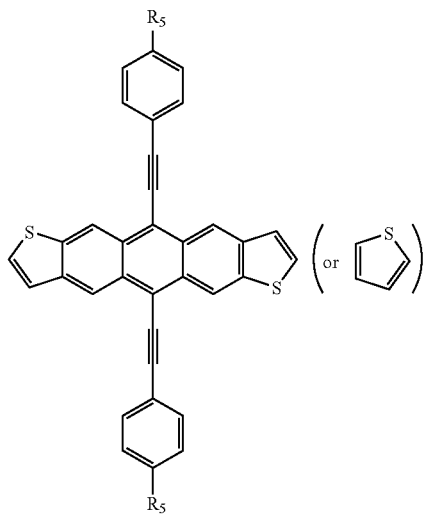
(9)
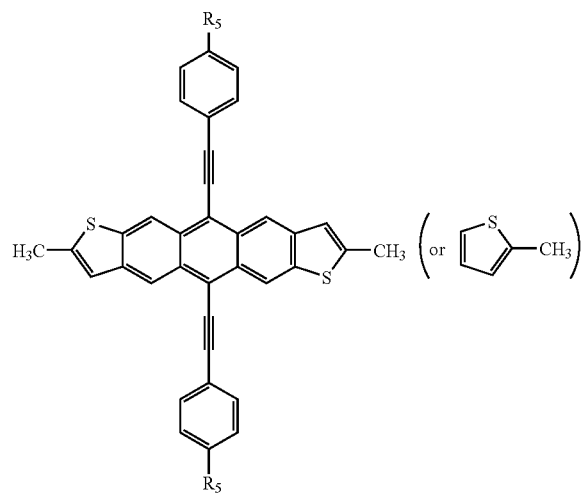
(10)
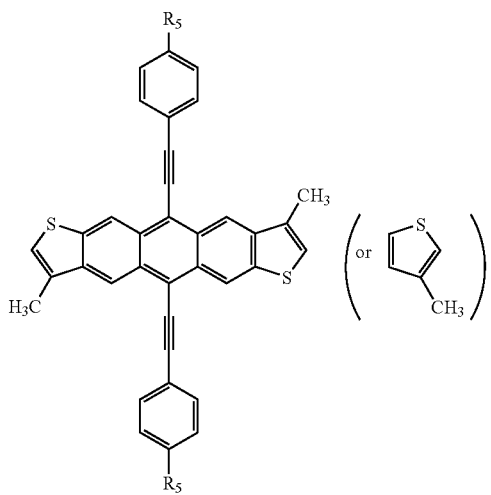

-continued
(11) 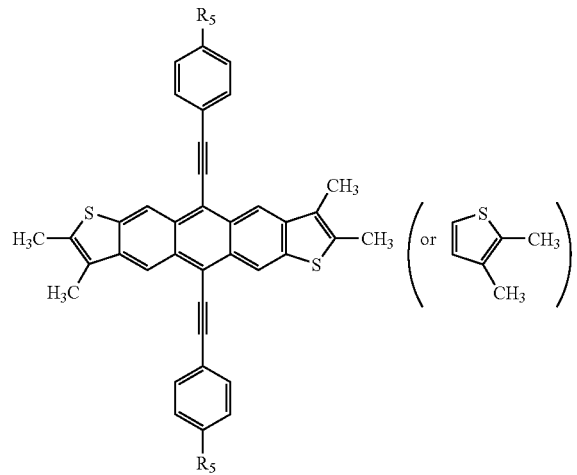
(12) 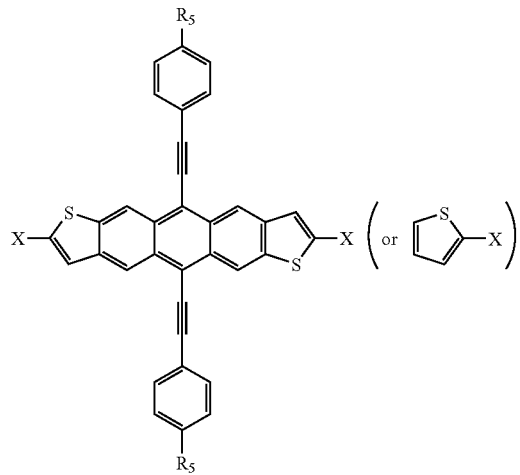
(13) 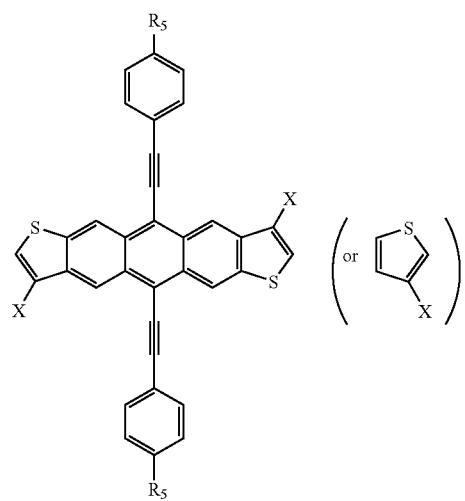
(14) 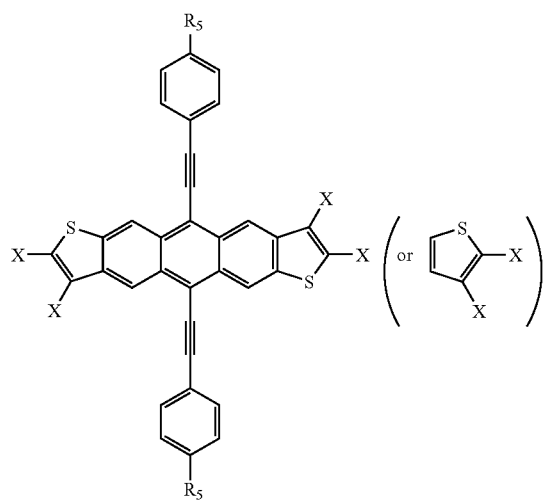
(15) 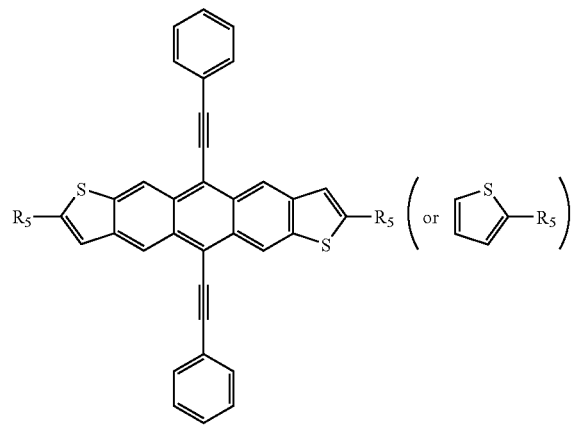
(16) 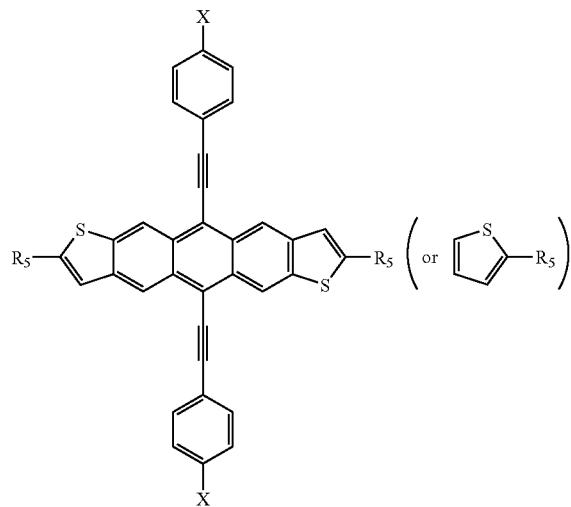

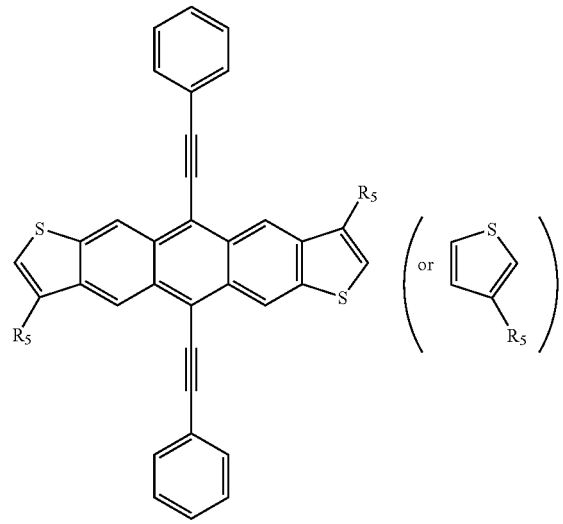
(17)
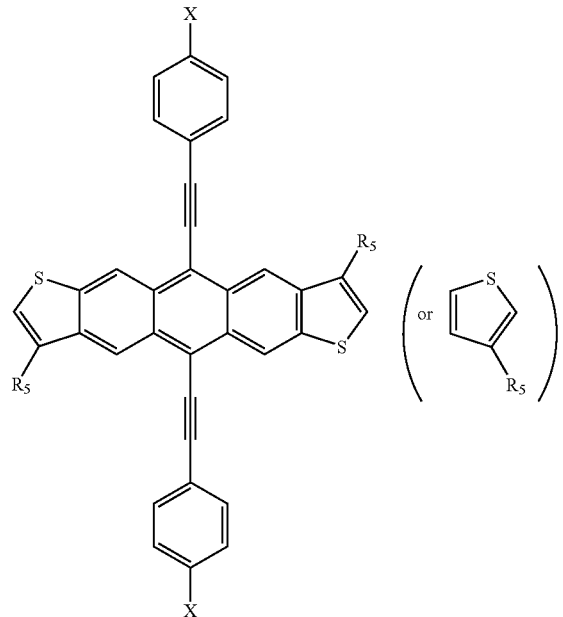
(18)
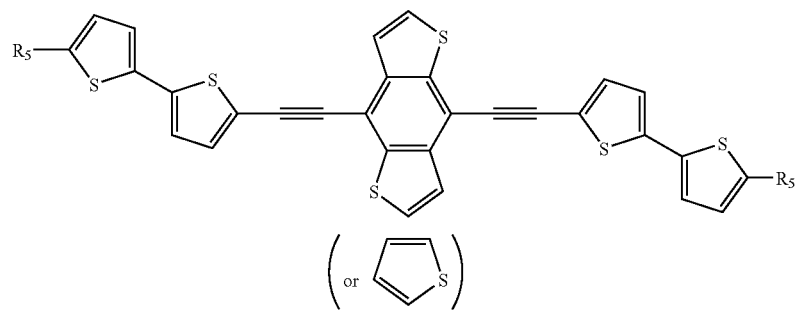
(19)
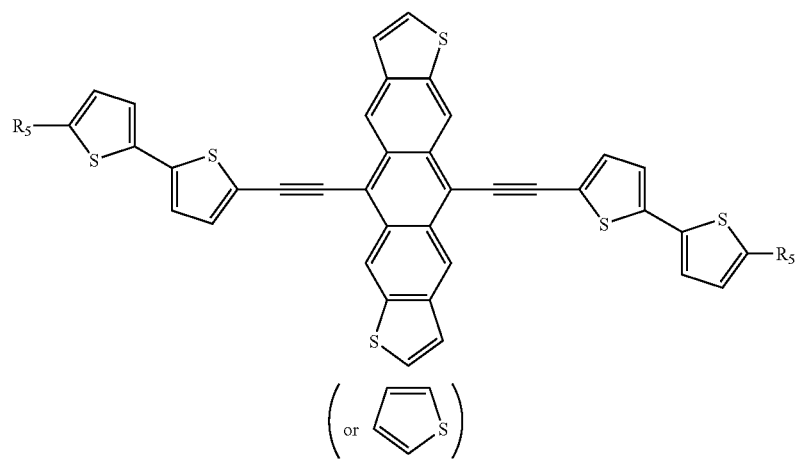
(20)

-continued
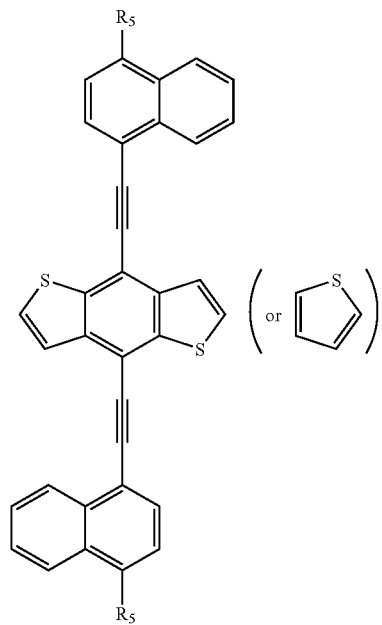
(21)
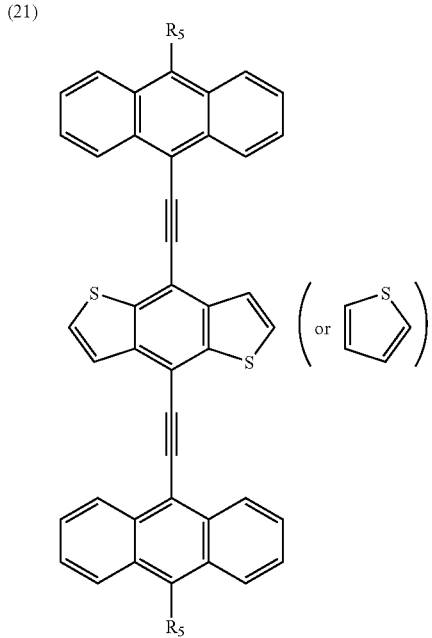
(22)
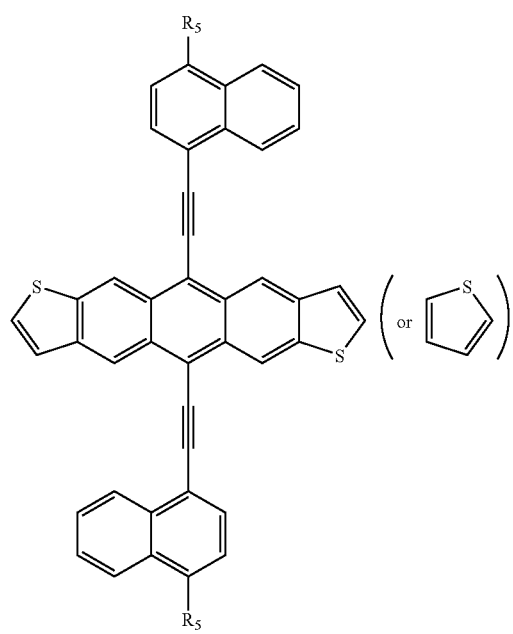
(23)
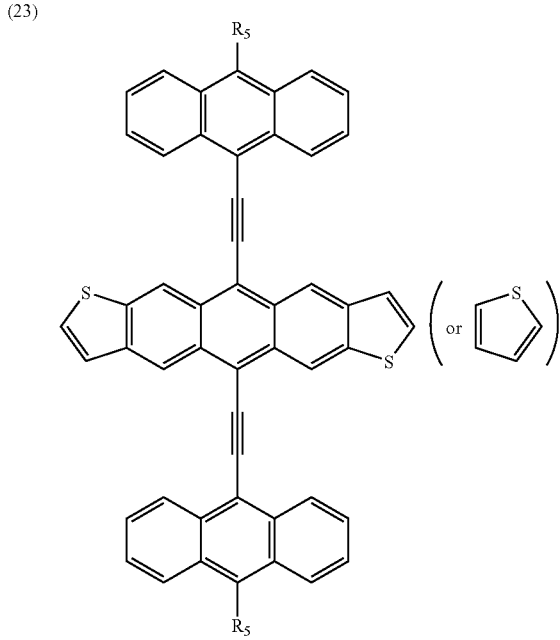
(24)

-continued

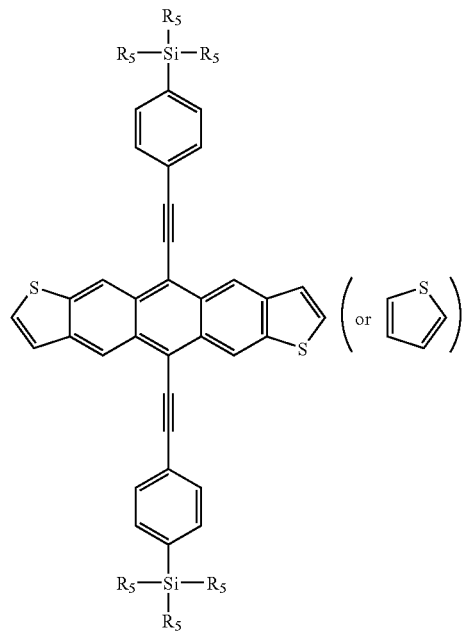
(25)

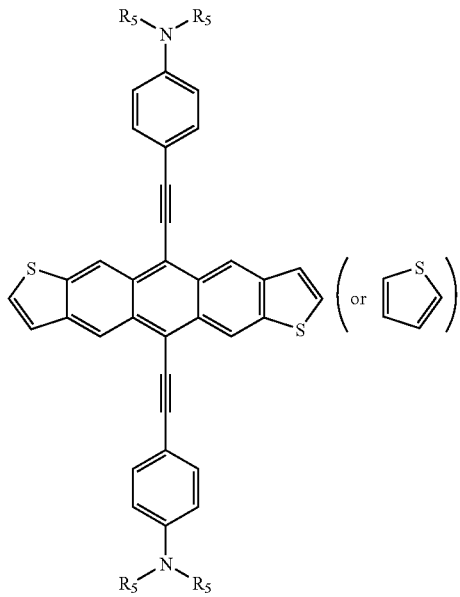
(26)

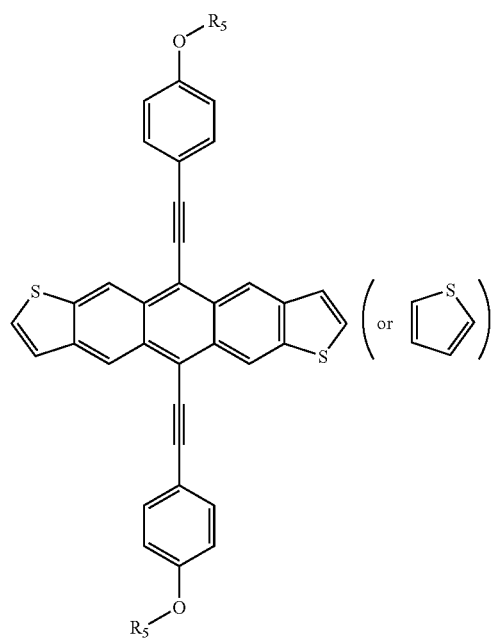
(27)

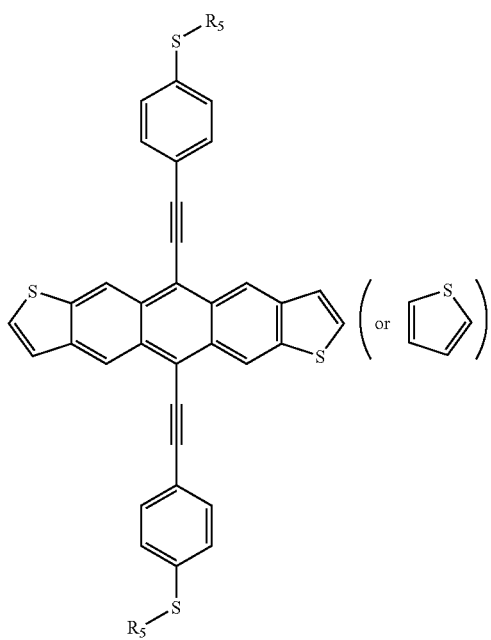
(28)

wherein $R_5$ is, for example, a hydrocarbon of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, or octadecyl; trifluoromethyl, fluoroethyl, perfluoropropyl, perfluorobutyl, perfluoropentyl, perfluorohexyl, perfluoroheptyl, perfluorooctyl, perfluorononyl, perfluorodecyl, perfluoroundecyl, or perfluorododecyl; phenyl, methylphenyl (tolyl), ethylphenyl, propylphenyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, trifluoromethylphenyl, fluoroethylphenyl, perfluoropropylphenyl, perfluorobutylphenyl, perfluoropentylphenyl, perfluorohexylphenyl, perfluoroheptylphenyl, perfluorooctylphenyl, perfluorononylphenyl, perfluorodecylphenyl, perfluoroundecylphenyl, or perfluorododecylphenyl; and wherein X is F, Cl, Br, CN, or $NO_2$.

The polymers, such as the functionalized heteroacenes, in embodiments are soluble or substantially soluble in common coating solvents, for example, in embodiments they possess a solubility of at least about 0.1 percent by weight, and more specifically, from about 10 percent to about 95 percent by weight in such solvents as methylene chloride, 1,2-dichloroethane, tetrahydrofuran, toluene, xylene, mesitylene, chlorobenzene, dichlorobenzene, and the like. Moreover, the functionalized heteroacenes of the present disclosure in embodiments when fabricated as semiconductor channel layers in TFT devices provide a stable conductivity of, for example, from about $10^{-9}$ S/cm to about $10^{-4}$ S/cm, and more specifically, from about $10^{-8}$ S/cm to about $10^{-5}$ S/cm as determined by conventional four-probe conductivity measurements.

are, therefore, simpler and more cost effective, and the fabrication thereof can be applied to large scale production processes.

The preparation of functionalized heteroacenes of the present disclosure can be generally accomplished as illustrated herein. More specifically, one process of preparation is illustrated in Scheme 1.

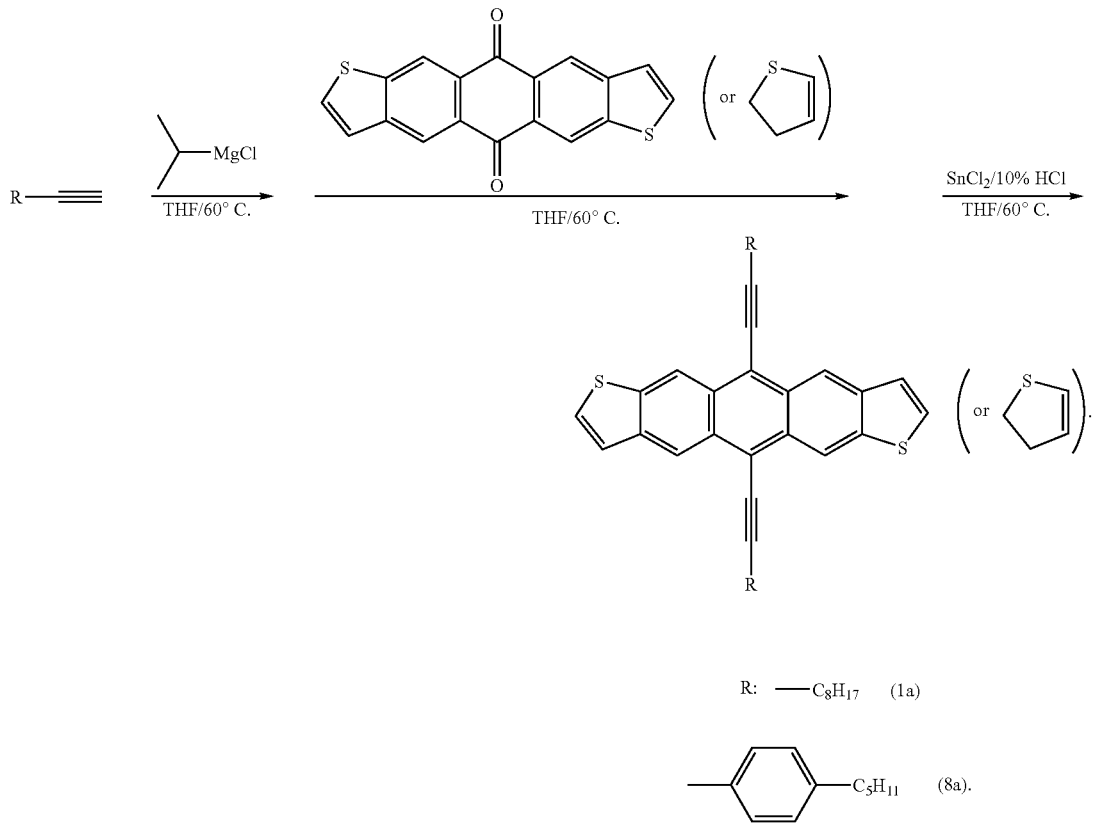

It is believed that the polymers when fabricated from solutions as thin films, for example, of from about 10 nanometers to about 500 nanometers or from about 100 to about 300 nanometers in thickness materials are more stable in ambient conditions than similar devices fabricated from heteroacenes. When unprotected, the aforementioned polymer materials and devices are generally stable for a number of weeks rather than days or hours as is the situation with poly(3-alkylthiophene-2,5-diyl) after exposure to ambient oxygen, thus the devices fabricated from the functionalized heteroacenes in embodiments of the present disclosure can provide higher current on/off ratios, and their performance characteristics do not substantially change as rapidly as that of nonfunctionalized heteroacenes, or than poly(3-alkylthiophene-2,5-diyl) when no rigorous procedural precautions have been taken to exclude ambient oxygen during material preparation, device fabrication, and evaluation. The functionalized heteroacenes stability of the present disclosure in embodiments against oxidative doping, particularly for low cost device manufacturing, does not usually have to be handled in an inert atmosphere, and the processes thereof 5,11-Decynylanthra[2,3-b:6,7-b']dithiophene/5,11-decynylanthra[2,3-b:7,6-b']dithiophene (1a, a mixture of trans and cis isomers) and 5,11-bis(4-phenylethynyl)anthra[2,3-b:6,7-b']dithiophene/5,11-bis(4-phenylethynyl)anthra[2,3-b:7,6-b']dithiophene (8a, a mixture of trans and cis isomers) can be generated as shown in Scheme 1. First, 1-decyne (available from Sigma-Aldrich) is reacted with about 1 molar equivalent of isopropylmagnesium chloride (available from Sigma-Aldrich) in tetrahydrofuran (THF) at elevated temperatures of, for example, 60° C. for a suitable period like 30 minutes. Then to the reaction mixture is added anthra[2,3-b:6,7-b']dithiophene-5,11-dione/anthra[2,3-b:7,6-b']dithiophene-5,11-dione (a mixture of trans and cis isomers) (this starting material is prepared according to De la Cruz, P., et al, *J. Org. Chem.* 1992, 57, 6192) followed by stirring at elevated temperatures of, for example, 60° C. for a suitable period like 1 hour. Finally, tin (II) chloride ($SnCl_2$) solution in 10 percent HCl is added to the reaction mixture and stirred at elevated temperatures of, for example, 60° C. for a suitable period like 30 minutes. After work up and recrystallization, the substantially pure compound 1a is obtained. Compound 8a is prepared similarly starting from 1-ethynyl-4-pentylbenzene (available from Sigma-Aldrich) instead of 1-decyne.

Aspects of the present disclosure relate to an electronic device containing the functionalized heteroacenes illustrated herein; a device which is a thin film transistor comprised of a substrate, a gate electrode, a gate dielectric layer, a source electrode and a drain electrode, and in contact with the source/drain electrodes and the gate dielectric layer, a semiconductor layer comprised of the functionalized heteroacenes illustrated herein, and more specifically, an electronic device comprising a semiconductive material containing a component of Formula (I)

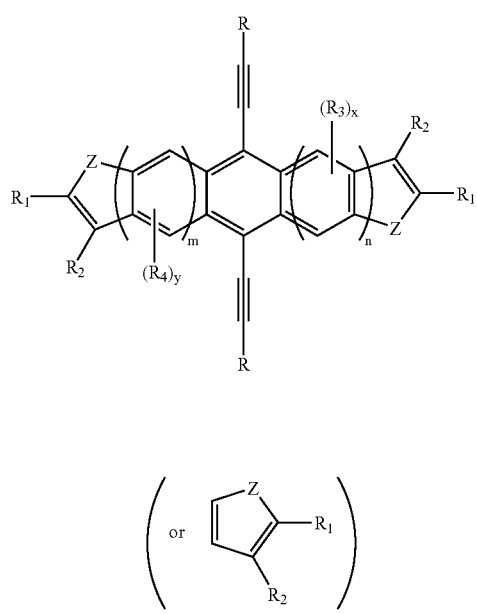

(I)

wherein R represents alkyl, aryl, or heteroaryl; each $R_1$ and $R_2$ is independently hydrogen (H), a suitable hydrocarbon, a heteroatom containing group or a halogen; $R_3$ and $R_4$ are independently a suitable hydrocarbon, a heteroatom containing group, or a halogen; x and y represent the number of groups; Z represents sulfur, oxygen, selenium, or NR' wherein R' is hydrogen, alkyl, or aryl; and n and m represent the number of repeating units; a thin film transistor comprised of a substrate, a gate electrode, a gate dielectric layer, a source electrode and a drain electrode, and in contact with the source/drain electrodes and the gate dielectric layer a semiconductor layer comprised of components of the formula

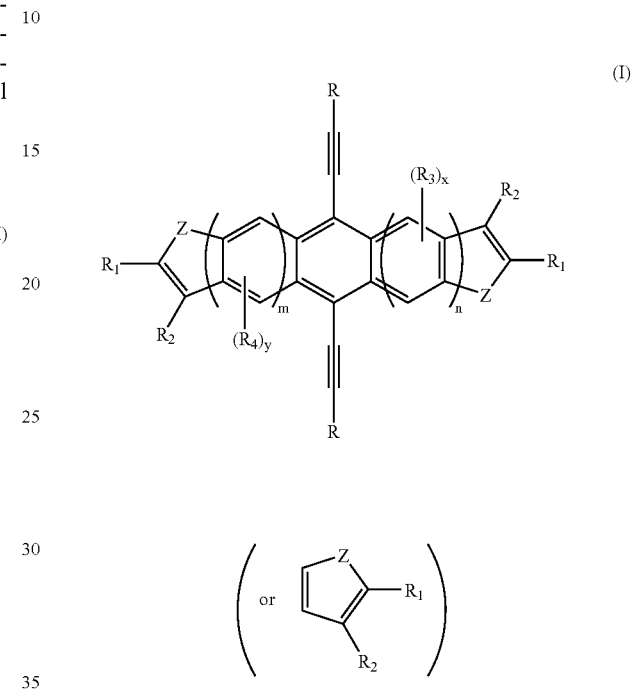

(I)

wherein R represents a hydrocarbon; each $R_1$ and $R_2$ is independently hydrogen (H), a suitable hydrocarbon; a heteroatom containing group or a halogen; $R_3$ and $R_4$ are independently a suitable hydrocarbon, a heteroatom containing group, or a halogen; x, and y represent the number of groups; Z represents sulfur, oxygen, selenium, or NR' wherein R' is hydrogen, alkyl, or aryl; and m and n represent the number of rings; a thin film transistor comprised of a substrate, a gate electrode, a gate dielectric layer, a source electrode, a drain electrode and a layer of a functionalized heteroacene of the formulas

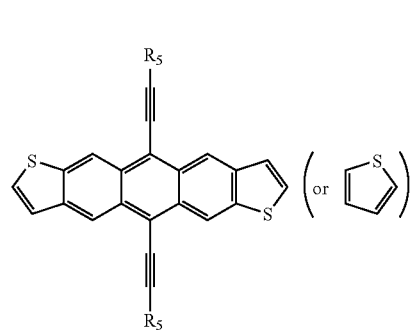

-continued
(3)
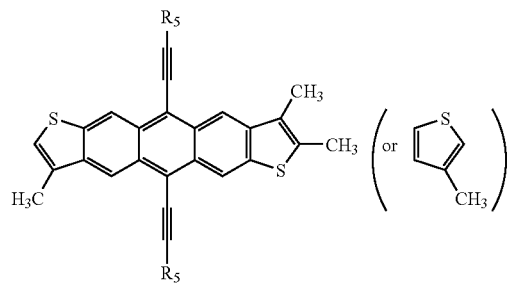
(4)
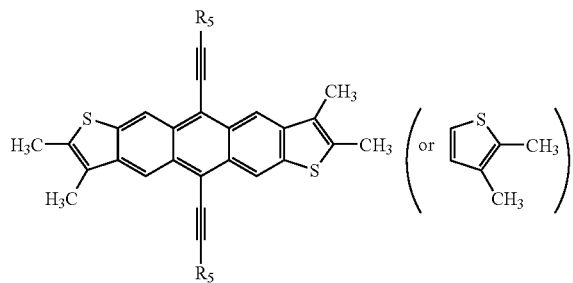
(5)
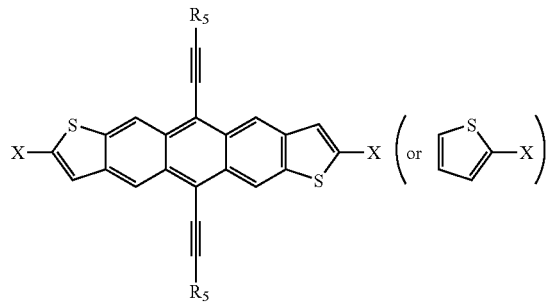
(6)
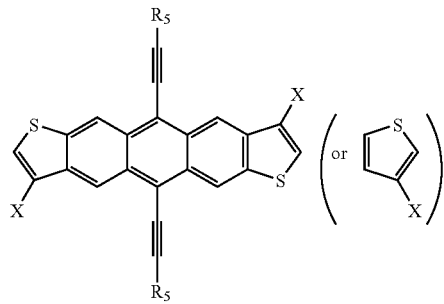
(7)
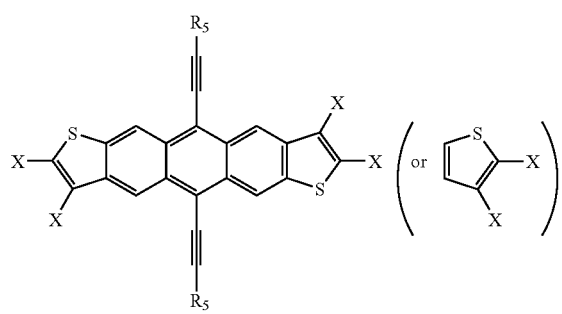
(8)
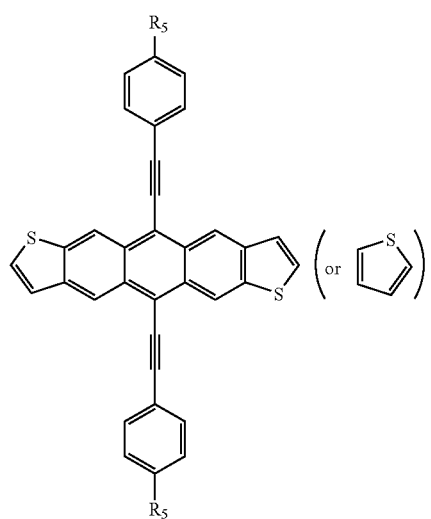

-continued
(9)
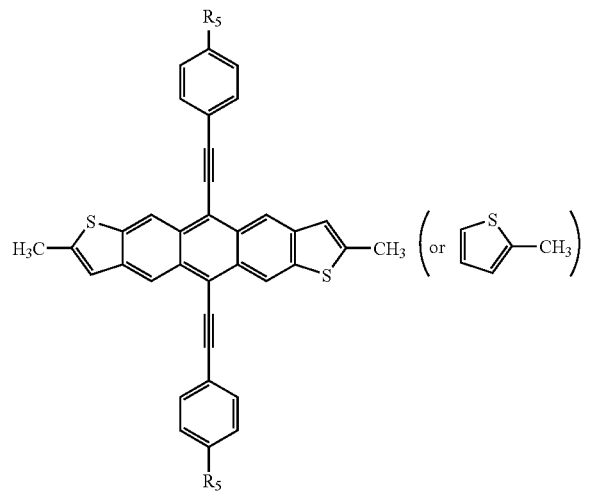
(10)
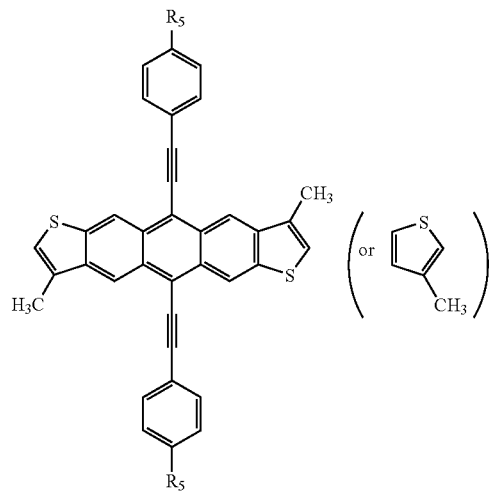
(11)
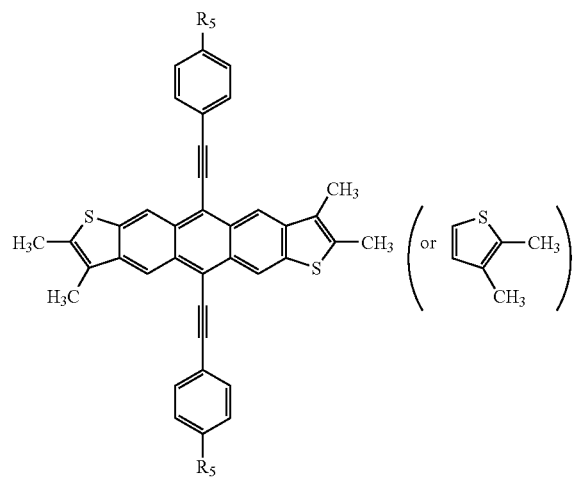
(12)
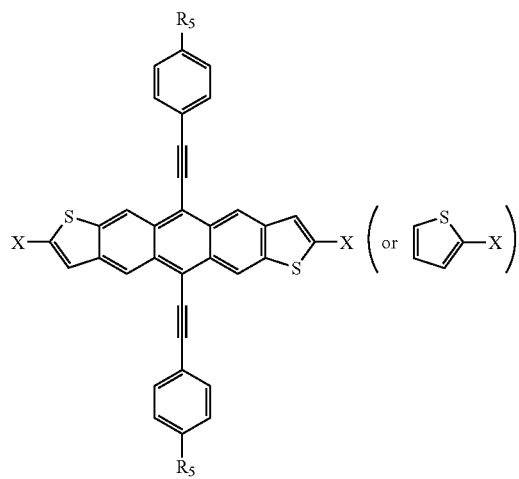
(13)
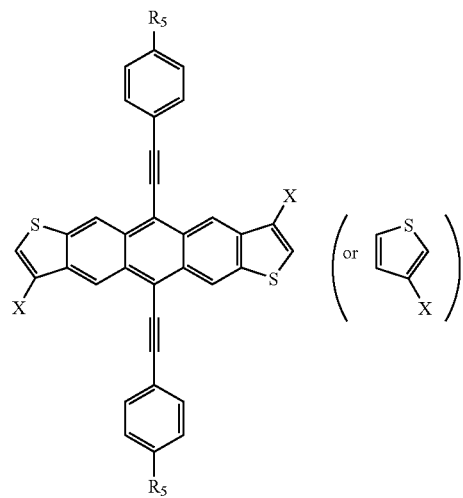
(14)
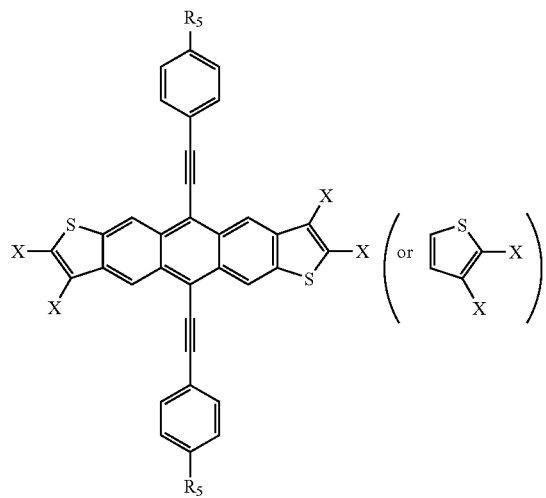

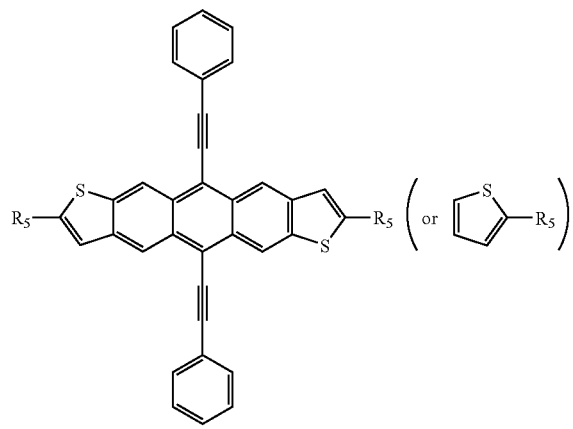
(15)
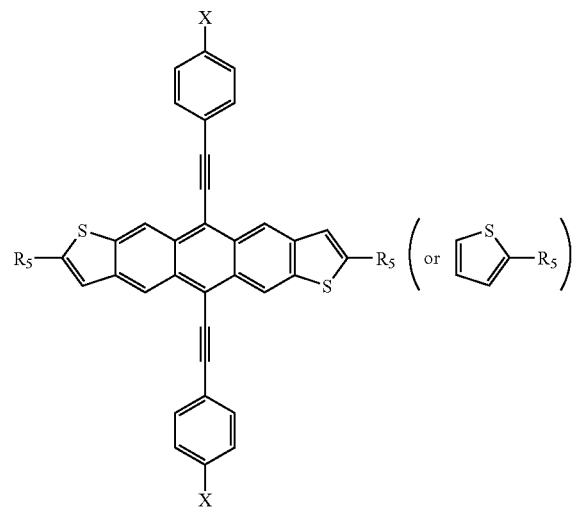
(16)
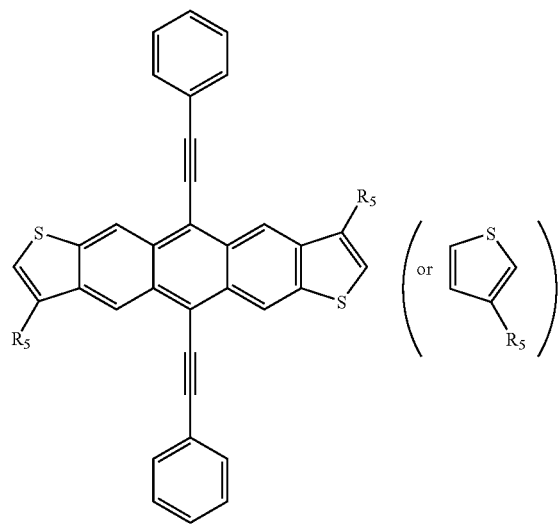
(17)
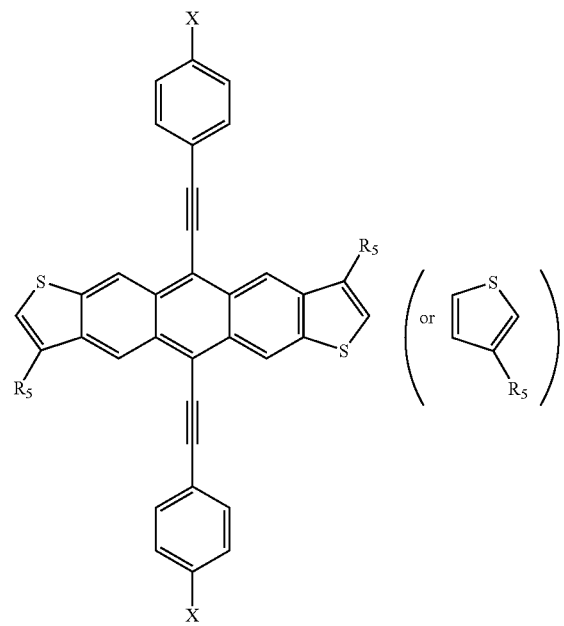
(18)
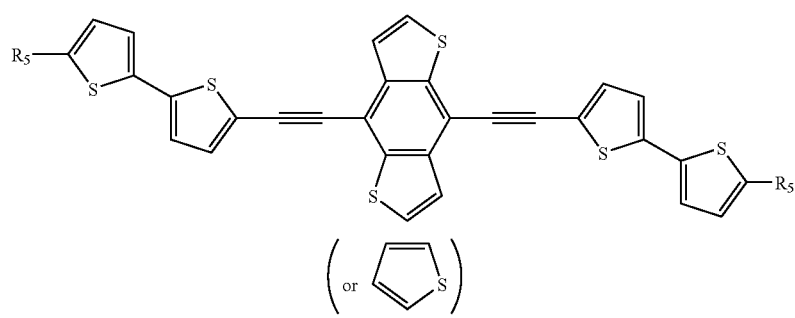
(19)

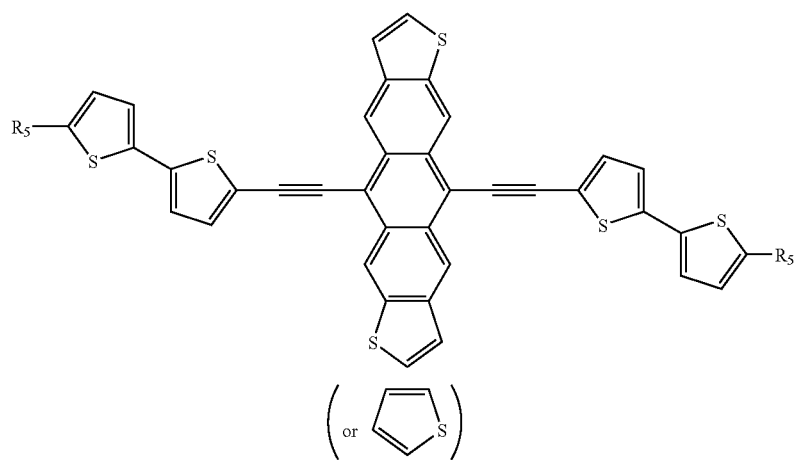
(20)
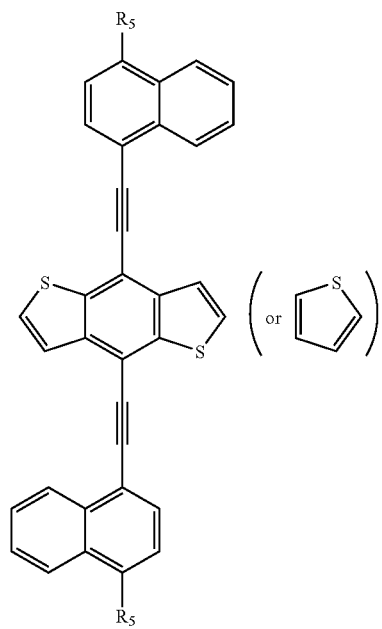
(21)
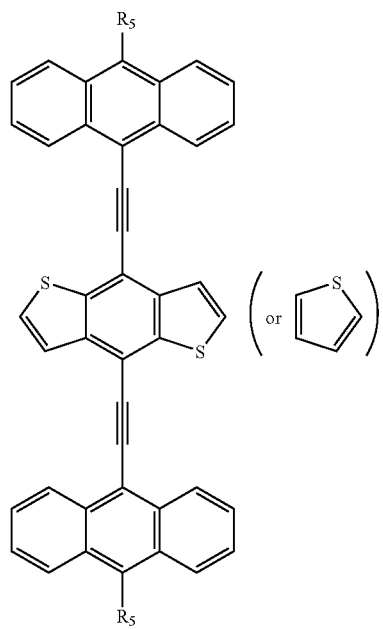
(22)

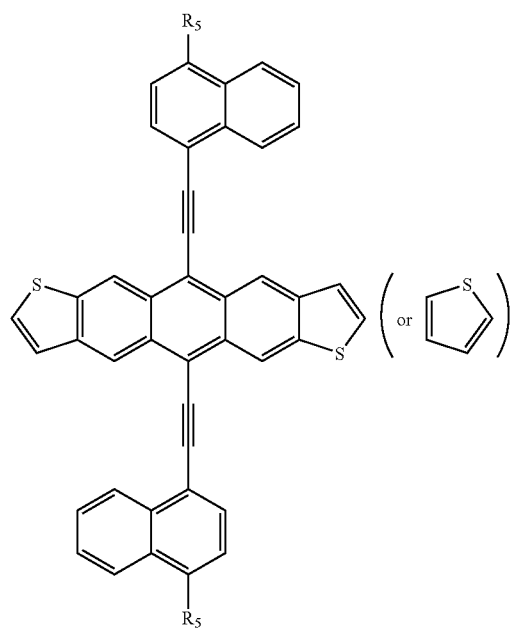
(23)
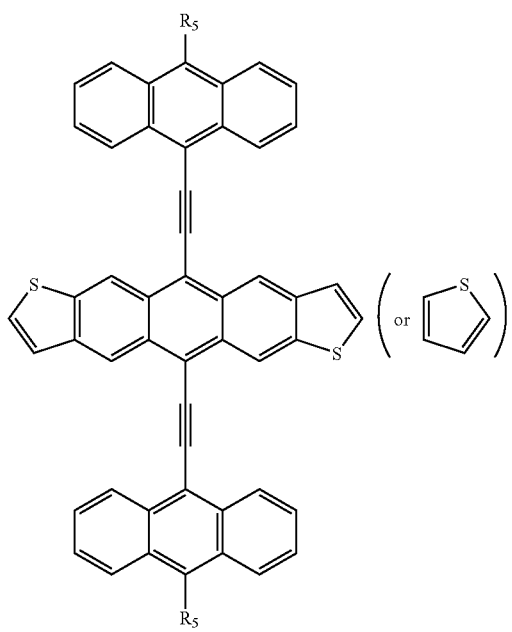
(24)
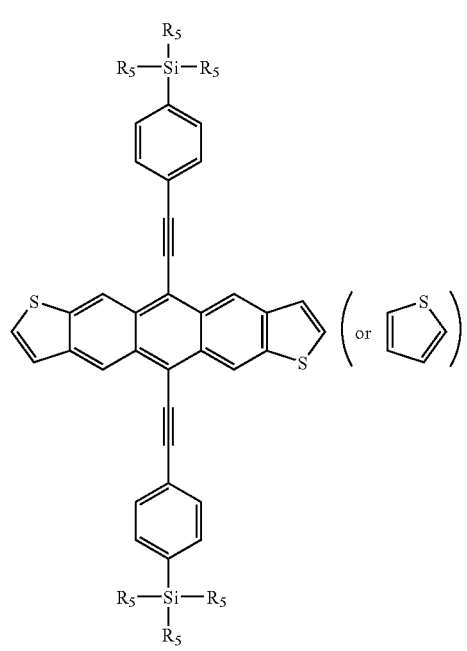
(25)
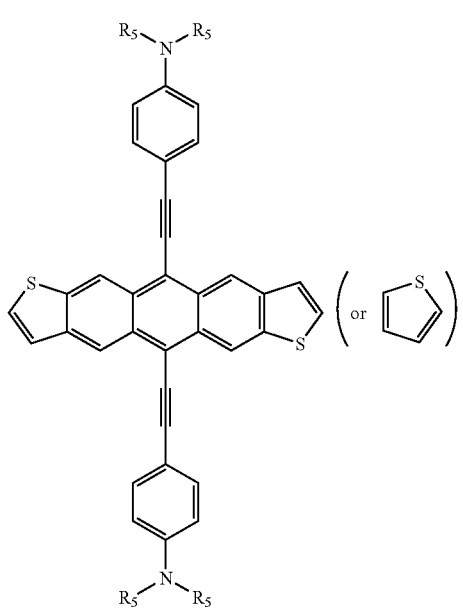
(26)

-continued

(27)
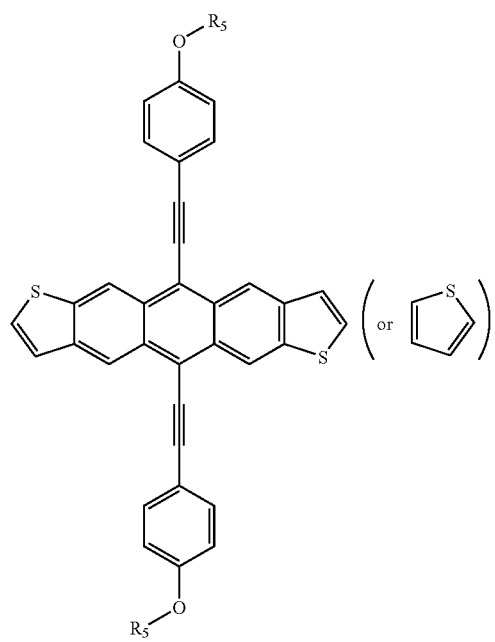

(28)
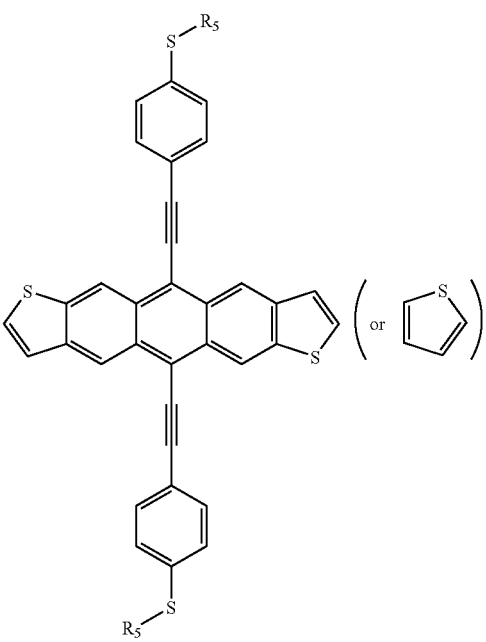

wherein R₅ is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, or octadecyl; trifluoromethyl, fluoroethyl, perfluoropropyl, perfluorobutyl, perfluoropentyl, perfluorohexyl, perfluoroheptyl, perfluorooctyl, perfluorononyl, perfluorodecyl, perfluoroundecyl, or perfluorododecyl; phenyl, methylphenyl (tolyl), ethylphenyl, propylphenyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, trifluoromethylphenyl, fluoroethylphenyl, perfluoropropylphenyl, perfluorobutylphenyl, perfluoropentylphenyl, perfluorohexylphenyl, perfluoroheptylphenyl, perfluorooctylphenyl, perfluorononylphenyl, perfluorodecylphenyl, perfluoroundecylphenyl, or perfluorododecylphenyl; and wherein X is F, Cl, Br, CN, or NO₂; a polymer of the formula/structure (I)
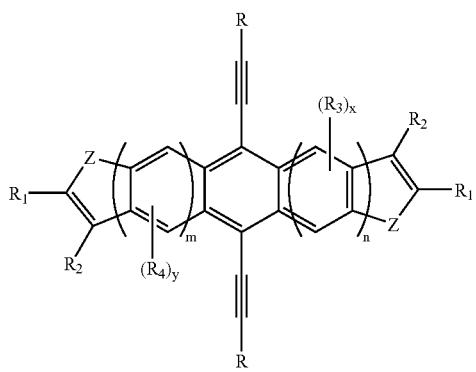

-continued

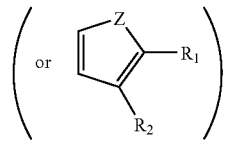

wherein R represents alkyl, aryl, or heteroaryl; each $R_1$ and $R_2$ is independently hydrogen (H), a suitable hydrocarbon; a heteroatom containing group or a halogen; $R_3$ and $R_4$ are independently a suitable hydrocarbon, a heteroatom containing group, or a halogen; x and y represent the number of groups; Z represents sulfur, oxygen, selenium, or NR' wherein R' is hydrogen, alkyl, or aryl; and n and m represent the number of repeating unit; a TFT device wherein the substrate is a plastic sheet of a polyester, a polycarbonate, or a polyimide; the gate source and drain electrodes are each independently comprised of gold, nickel, aluminum, platinum, indium titanium oxide, or a conductive polymer, and the gate dielectric is a dielectric layer comprised of silicon nitride or silicon oxide; a TFT device wherein the substrate is glass or a plastic sheet; said gate, source and drain electrodes are each comprised of gold, and the gate dielectric layer is comprised of the organic polymer poly(methacrylate), or poly(vinyl phenol); a device wherein the functionalized heteroacene layer is formed by solution processes of spin coating, stamp printing, screen printing, or jet printing; a device wherein the gate, source and drain electrodes, the gate dielectric, and semiconductor layers are formed by solution processes of spin coating, solution casting, stamp printing, screen printing, or jet printing; and a TFT device wherein the substrate is a plastic sheet of a polyester, a polycarbonate, or a polyimide, and the gate, source and drain electrodes are fabricated from the organic conductive polymer polystyrene sulfonate doped poly(3,4-ethylene dioxythiophene), or from a conductive ink/paste compound of a colloidal dispersion of silver in a polymer binder, and the gate dielectric layer is organic polymer or inorganic oxide particle-polymer composite; and device or devices include electronic devices such as TFTs.

DETAILED DESCRIPTION OF THE FIGURES

In FIG. 1 there is schematically illustrated a TFT configuration 10 comprised of a substrate 16, in contact therewith a metal contact 18 (gate electrode), and a layer of an insulating dielectric layer 14 with the gate electrode having a portion thereof or the entire gate in contact with the dielectric layer 14 on top of which layer 14 two metal contacts, 20 and 22 (source and drain electrodes), are deposited. Over and between the metal contacts 20 and 22 is the polymer layer 12 of 5,11-decynylanthra[2,3-b:6,7-b']dithiophene/5,11-decynylanthra[2,3-b:7,6-b']dithiophene (1a), a mixture of the cis and trans isomers thereof. The gate electrode can be included in the substrate, in the dielectric layer, and the like throughout.

Figure 2:
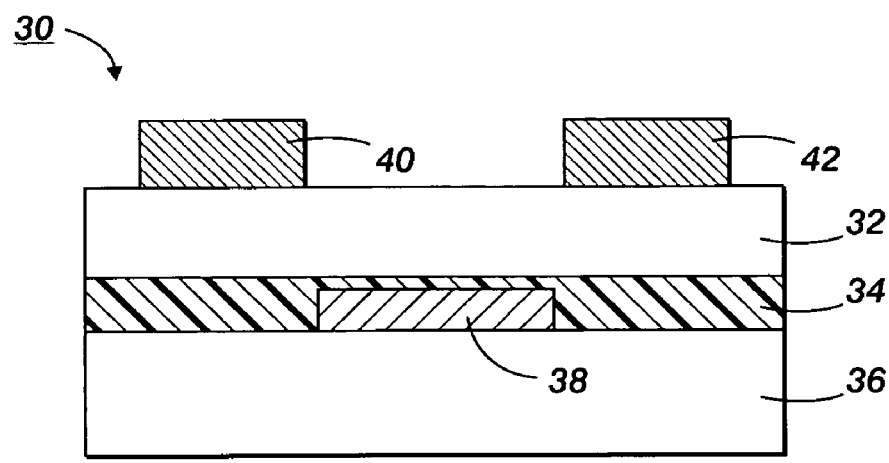

FIG. 2 schematically illustrates another TFT configuration 30 comprised of a substrate 36, a gate electrode 38, a source electrode 40, and a drain electrode 42, an insulating dielectric layer 34, and a functionalized heteroacene semiconductor layer 32 of 5,11-bis(4-phenylethynyl)anthra[2,3-b:6,7-b']dithiophene/5,11-bis(4-phenylethynyl)anthra[2,3-b:7,6-b']dithiophene (8a), a mixture of the cis and trans isomers thereof.

Figure 3:
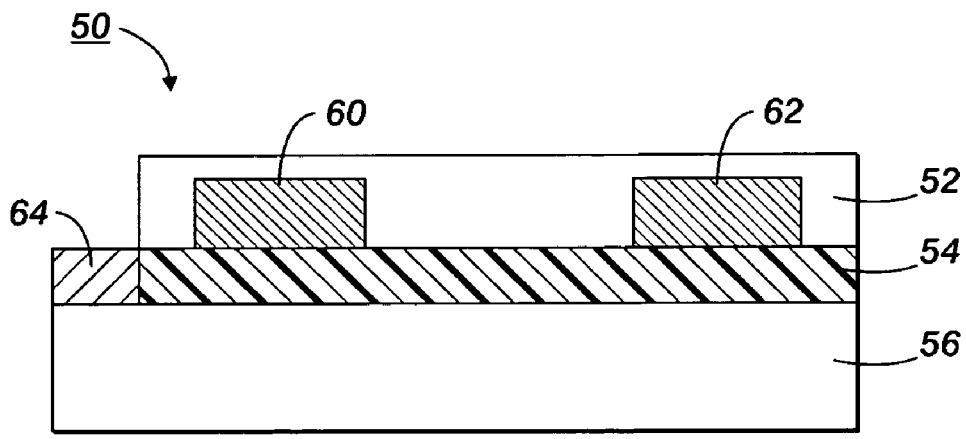

FIG. 3 schematically illustrates a further TFT configuration 50 comprised of a heavily n-doped silicon wafer 56, which can act as a gate electrode, a thermally grown silicon oxide dielectric layer 54, the functionalized heteroacene semiconductor layer 52 of FIG. 2, on top of which are deposited a source electrode 60 and a drain electrode 62; and a gate electrode contact 64.

Figure 4:
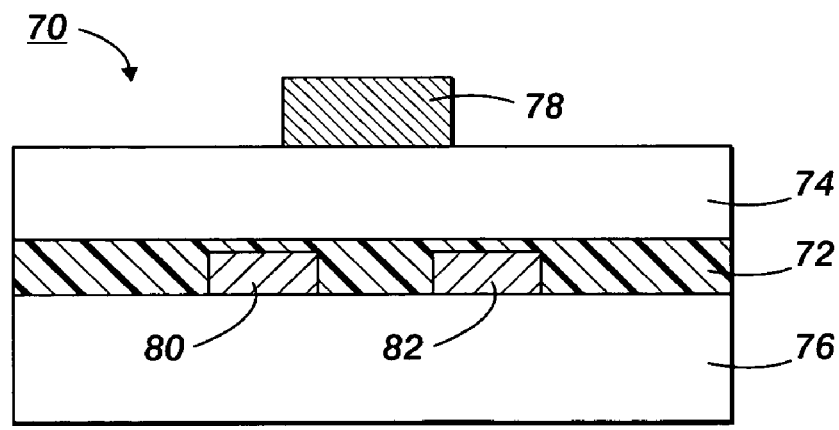

FIG. 4 schematically illustrates a TFT configuration 70 comprised of substrate 76, a gate electrode 78, a source electrode 80, a drain electrode 82, a functionalized heteroacene semiconductor layer 72 of FIG. 2, and an insulating dielectric layer 74.

Also, other devices not disclosed, especially TFT devices, are envisioned, reference for example known TFT devices.

In some embodiments of the present disclosure, an optional protecting layer may be incorporated on top of each of the transistor configurations of FIGS. 1, 2, 3 and 4. For the TFT configuration of FIG. 4, the insulating dielectric layer 74 may also function as a protecting layer.

Also disclosed are semiconductors of thiopheneacenes of the following formula

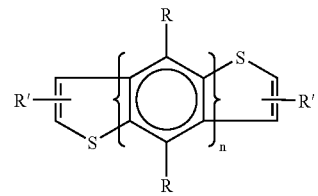

wherein R and R' are hydrogen, alkyl, unsaturated alkyl, aryl, alkyl substituted aryl, unsaturated alkyl substituted aryl, or mixtures thereof, and wherein n represents the number of rings of, for example, equal to or greater than 3, such as from about 3 to about 2,000, and more specifically, wherein n=5, R'=H, and R=dodycyne.

These novel organic semiconductors, such as for use in TFTs, can be prepared by the following reaction scheme Scheme 2

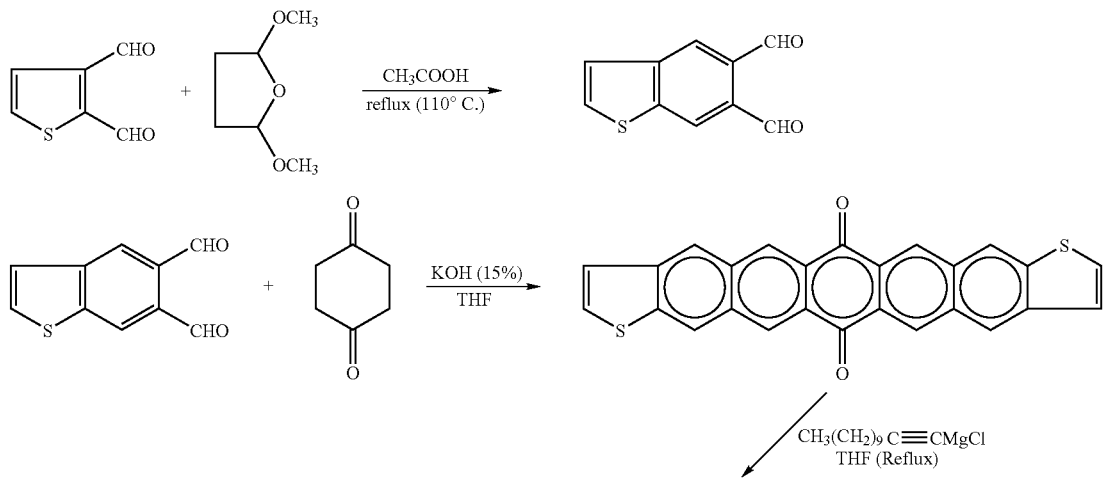

-continued

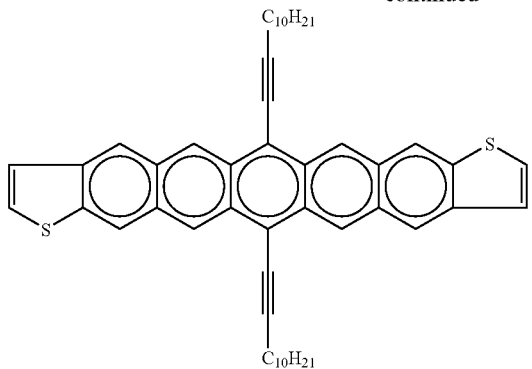

(2)

The final product was greenish and it showed a UV maximum peak at a wavelength of 740 nanometers. The UV spectra data for the maximum peak absorbance at 740 nanometers are listed in Table 1. It showed that the solution of structure (2) is more stable in the ambient condition than pentacene.

TABLE 1

UV SPECTRA DATA FOR THE STRUCTURE (2) IN THF

| Time (Min.) | Maximum Wavelength ($\lambda$, nm) | Absorbance | Stability |
|---|---|---|---|
| 1 | 740 | 1.193 | 100% |
| 10 | 740 | 1.163 | 97.5% |
| 20 | 740 | 1.121 | 94.0% |
| 30 | 740 | 1.080 | 90.5% |

In embodiments and with further reference to the present disclosure and the Figures, the device substrate layer may generally be a silicon material inclusive of various appropriate forms of silicon, a glass plate, a plastic film or a sheet, and the like depending on the intended applications. For structurally flexible devices, a plastic substrate, such as for example polyester, polycarbonate, polyimide sheets, and the like, may be selected. The thickness of the substrate may be, for example, from about 10 micrometers to over 10 millimeters with a specific thickness being from about 50 to about 100 micrometers, especially for a flexible plastic sustrate, and from about 1 to about 10 millimeters for a rigid substrate, such as glass or silicon.

The insulating dielectric layer, which can separate the gate electrode from the source and drain electrodes, and in contact with the semiconductor layer, can generally be an inorganic material film, an organic polymer film, or an organic-inorganic composite film. The thickness of the dielectric layer is, for example, from about 10 nometers to about 1 micrometer with a more specific thickness being about 100 nometers to about 500 nanometers. Illustrative examples of inorganic materials suitable as the dielectric layer include silicon oxide, silicon nitride, aluminum oxide, barium titanate, barium zirconate titanate, and the like; illustrative examples of organic polymers for the dielectric layer include polyesters, polycarbonates, poly(vinyl phenol), polyimides, polystyrene, poly(methacrylate)s, poly(acrylate)s, epoxy resin, and the like; and illustrative examples of inorganic-organic composite materials include nanosized metal oxide particles dispersed in polymers such as polyester, polyimide, epoxy resin and the like. The insulating dielectric layer is generally of a thickness of from about 50 nanometers to about 500 nanometers depending on the dielectric constant of the dielectric material used. More specifically, the dielectric material has a dielectric constant of, for example, at least about 3, thus a suitable dielectric thickness of about 300 nanometers can provide a desirable capacitance, for example, of about $10^{-9}$ to about $10^{-7}$ F/cm$^2$.

Situated, for example, between and in contact with the dielectric layer and the source/drain electrodes is the active semiconductor layer comprised of the functionalized heteroacenes illustrated herein, and wherein the thickness of this layer is generally, for example, about 10 nanometers to about 1 micrometer, or about 40 to about 100 nanometers. This layer can generally be fabricated by solution processes, such as spin coating, casting, screen, stamp, or jet printing of a solution of the functionalized heteroacenes of the present disclosure.

The gate electrode can be a thin metal film, a conducting polymer film, a conducting film generated from a conducting ink or paste, or the substrate itself (for example, heavily doped silicon). Examples of gate electrode materials include but are not limited to aluminum, gold, chromium, indium tin oxide, conducting polymers, such as polystyrene sulfonate-doped poly(3,4-ethylenedioxythiophene) (PSS/PEDOT), a conducting ink/paste comprised of carbon black/graphite or colloidal silver dispersion contained in a polymer binder, such as Electrodag available from Acheson Colloids Company, and silver filled electrically conductive thermoplastic ink available from Noelle Industries, and the like. The gate layer can be prepared by vacuum evaporation, sputtering of metals or conductive metal oxides, coating from conducting polymer solutions or conducting inks, or dispersions by spin coating, casting or printing. The thickness of the gate electrode layer is, for example, from about 10 nanometers to about 10 micrometers, and a specific thickness is, for example, from about 10 to about 200 nanometers for metal films, and about 1 to about 10 micrometers for polymer conductors.

The source and drain electrode layer can be fabricated from materials which provide a low resistance ohmic contact to the semiconductor layer. Typical materials suitable for use as source and drain electrodes include those of the gate electrode materials, such as gold, nickel, aluminum, platinum, conducting polymers, and conducting inks. Typical thickness of this layer is, for example, from about 40 nanometers to about 1 micrometer with the more specific thickness being about 100 to about 400 nanometers. The TFT devices contain a semiconductor channel with a width W and length L. The semiconductor channel width may be, for example, from about 10 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of generally, for example, about 0 volt to about −80 volts is applied to the drain electrode to collect the charge carriers transported across the semiconductor channel when a voltage of generally about +10 volts to about −80 volts is applied to the gate electrode.

Other known materials not recited herein for the various components of the TFT devices of the present disclosure can also be selected in embodiments.

Although not desiring to be limited by theory, it is believed that the alkynyl like the ethynyl groups function primarily to minimize or avoid instability because of exposure to oxygen, and thus increase the oxidative stability of the heteroacenes in solution under ambient conditions, and the alkyl and/or alkylaryl substituents or groups permit the solubility of these compounds in common solvents, such as ethylene chloride. Also, in embodiments alkyl groups that are unbranched could facilitate the formation of layered pi-stacks, a favorable form for charge transport properties.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

What is claimed is:

1. An electronic device comprising a semiconductive material containing a component of Formula (I)

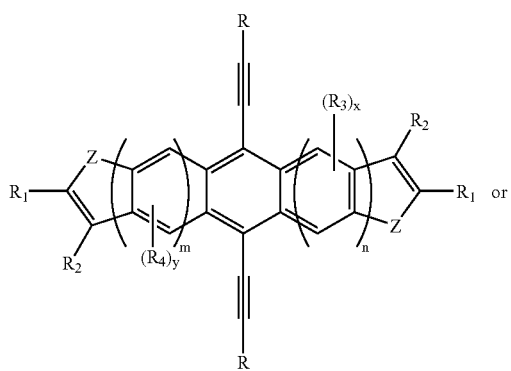

or

-continued

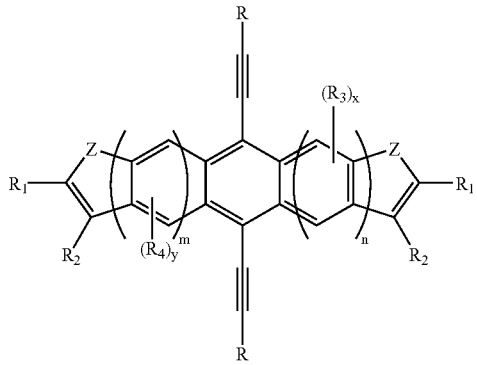

wherein R represents alkyl, alkoxy, aryl, or heteroaryl; each $R_1$ and $R_2$ is independently hydrogen (H), alkyl, aryl, a heteroatom containing group, cyano, nitro, or a halogen; $R_3$ and $R_4$ are independently alkyl, aryl, a heteroatom containing group, or a halogen; x and y represent the number of groups; Z represents sulfur, oxygen, selenium, or NR' wherein R' is hydrogen, alkyl, or aryl; and n and m represent the number of repeating units.

2. A device in accordance with claim 1 wherein R is aryl with from about 6 to about 48 carbon atoms.

3. A device in accordance with claim 1 wherein R is alkyl with from about 1 to about 25 carbon atoms.

4. A device in accordance with claim 1 wherein R is a heteroaryl with from about 7 to about 37 carbon atoms.

5. A device in accordance with claim 1 wherein at least one of $R_1$ and $R_2$ is hydrogen.

6. A device in accordance with claim 1 wherein at least one of $R_1$ and $R_2$ is alkyl.

7. A device in accordance with claim 1 wherein at least one of $R_1$ and $R_2$ is aryl.

8. A device in accordance with claim 1 wherein at least one of $R_1$ and $R_2$ is halogen.

9. A device in accordance with claim 1 wherein at least one of $R_1$ and $R_2$ is cyano or nitro.

10. A device in accordance with claim 1 wherein at least one of $R_3$ and $R_4$ is alkyl.

11. A device in accordance with claim 1 wherein at least one of $R_3$ and $R_4$ is aryl.

12. A device in accordance with claim 1 wherein said heteroatom containing group is dialkylamine, diarylamine, alkoxy, trialkylsilyl or triarylsilyl.

13. A device in accordance with claim 1 wherein said heteroatom containing group is thienyl, pyridyl, trialkylsilyl, triarylsilyl, or alkoxyalkoxyaryl.

14. A device in accordance with claim 1 wherein at least one of $R_1$, $R_2$, $R_3$, $R_4$ and R is alkyl.

15. A device in accordance with claim 1 wherein Z is sulfur, oxygen, or selenium.

16. A device in accordance with claim 1 wherein Z is NR' wherein R' is alkyl, or aryl.

17. A device in accordance with claim 1 wherein m is a number of from 0 to about 3.

18. A device in accordance with claim 1 wherein m is 2.

19. A device in accordance with claim 1 wherein m is 1.

20. A device in accordance with claim 1 wherein n is a number of from 0 to about 3.

21. A device in accordance with claim 1 wherein n is 1 or 2.

22. A device in accordance with claim 1 wherein x is a number of from 0 to about 12.

23. A device in accordance with claim 1 wherein x is a number of from 0 to about 6.

24. A device in accordance with claim 1 wherein y is a number of from 0 to about 12.

25. A device in accordance with claim 1 wherein y is a number of from 0 to about 4.

26. A device in accordance with claim 1 wherein R is aryl with 6 to about 36 carbon atoms; $R_1$ and $R_2$ are hydrogen; x=y=0; m and n are equal, and m is 1 or 2.

27. A thin film transistor comprised of a substrate, a gate electrode, a gate dielectric layer, a source electrode and a drain electrode, and in contact with the source/drain electrodes and the gate dielectric layer a semiconductor layer comprising a functionalized heteroacene of the formula

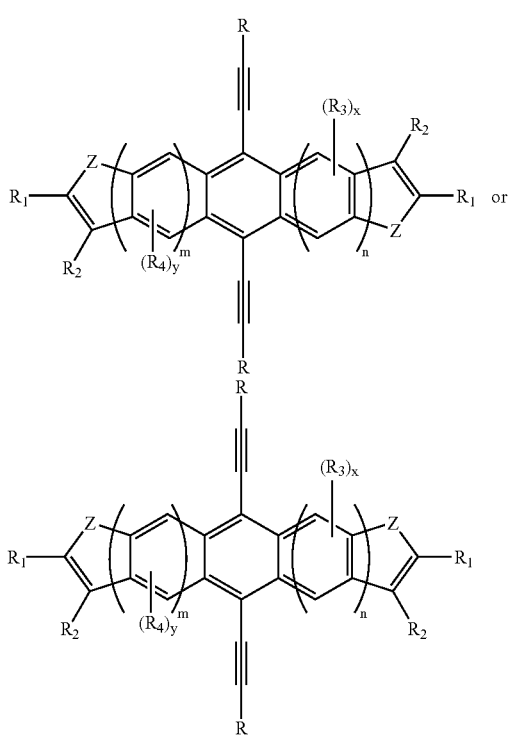

(I)

wherein R is alkyl, alkoxy, aryl, or heteroaryl; each $R_1$ and $R_2$ is independently hydrogen (H), alkyl, aryl, cyano, nitro, a heteroatom containing group or a halogen; $R_3$ and $R_4$ are independently alkyl, aryl, a heteroatom containing group, or a halogen; x, and y represent the number of groups; Z represents sulfur, oxygen, selenium, or NR' wherein R' is hydrogen, alkyl, or aryl; and m and n represent the number of rings.

28. A device in accordance with claim 27 wherein alkyl is ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, or eicosanyl.

29. A device in accordance with claim 27 wherein aryl is phenyl, tolyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, naphthyl, methylnaphthyl, ethylnaphthyl, propylnaphthyl, butylnaphthyl, pentylnaphthyl, hexylnaphthyl, heptylnaphthyl, octylnaphthyl, nonylnaphthyl, decylnaphthyl, undecylnaphthyl, dodecylnaphthyl, anthryl, methylanthryl, ethylanthryl, propylanthryl, butylanthryl, pentylanthryl, octylanthryl, nonylanthryl, decylanthryl, undecylanthryl, or dodecylanthryl.

30. A device in accordance with claim 27 wherein heteroaryl is thienyl, methylthienyl, ethylthienyl, propylthienyl, butylthienyl, hexylthienyl, heptylthienyl, octylthienyl, nonylthienyl, decylthienyl, undecylthienyl, dodecylthienyl, bithiophenyl, methylbithiophenyl, ethylbithiophenyl, propylbithiophenyl, propylbithiophenyl, butylbithiophenyl, pentylbithiophenyl, hexylbithiophenyl, heptylbithiophenyl, octylbithiophenyl, nonylbithiophenyl, decylbithiophenyl, undecylbithiophenyl, dodecylbithiophenyl, pyridyl, methylpyridyl, ethylpyridyl, propylpyridyl, butylpyridyl, pentylpyridyl, hexylpyridyl, heptylpyridyl, octylpyridyl, nonylpyridyl, decylpyridyl, undecylpyridyl, dodecylpyridyl, thiazolyl, methylthiazolyl, ethylthiazolyl, propylthiazolyl, butylthiazolyl, pentylthiazolyl, hexylthiazolyl, heptylthiazolyl, octylthiazolyl, nonylthiazolyl, decylthiazolyl, undecylthiazolyl, or dodecylthiazolyl.

31. A device in accordance with claim 27 wherein the functionalized heteroacene is selected from the group consisting of the following formulas

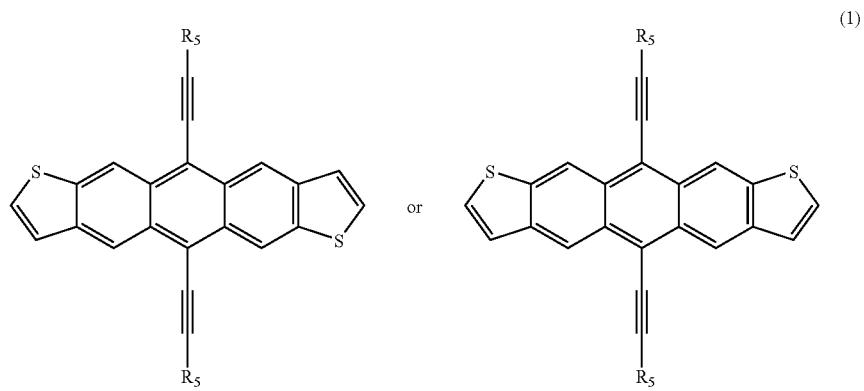

(1)

-continued
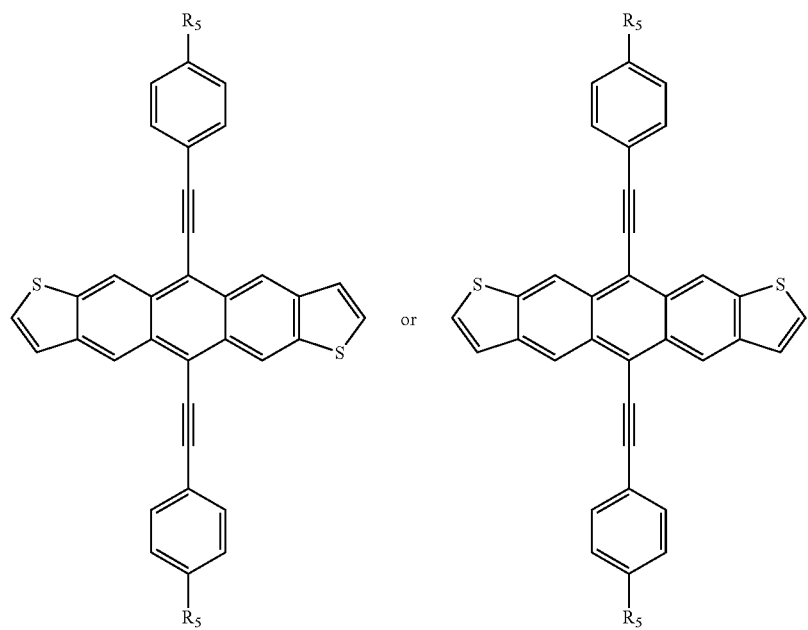 (8)
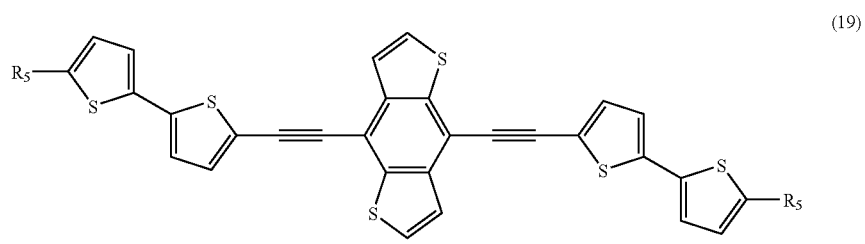 (19)
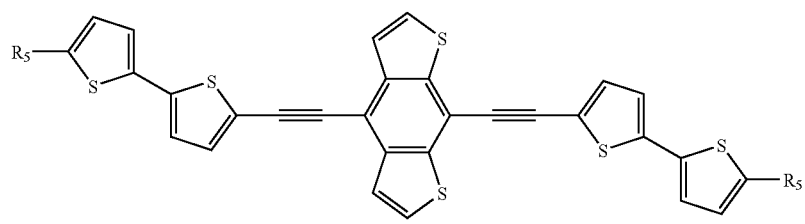
 (25)

-continued

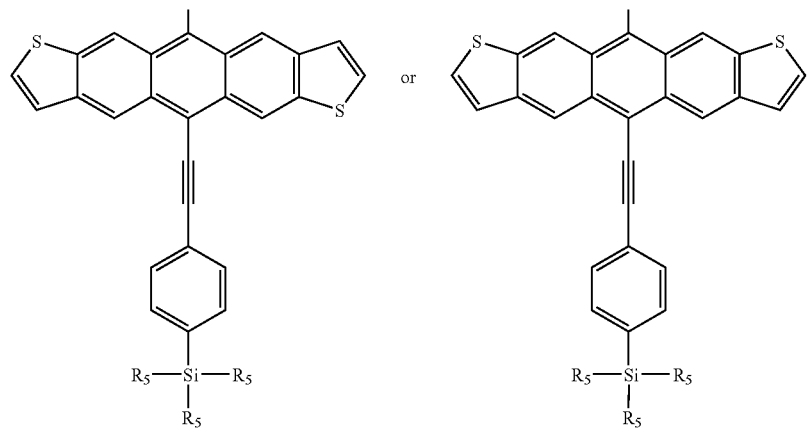

wherein $R_5$ is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, or octadecyl; trifluoromethyl, fluoroethyl, perflucropropyl, perfluorobutyl, pertluoropentyl, pert luorohexyl, perfluoroheptyl, pertluorooctyl, perfluorononyl, pereluorodecyl, pert luoroundecyl, or perfluorododecyl; phenyl, methylphenyl (tolyl), ethylphenyl, propylphenyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, trifluoromethylphenyl, fluoroethylphenyl, perluoropropylphenyl, perflucrobutylphenyl, pertluoropentylphenyl, pertluorohexylphenyl, pertluoroheptylphenyl, pertluorooctylphenyl, perfluorononylphenyl, perfluorodecylphenyl, pertluoroundecylphenyl, or pertluorododecylphenyl.

32. A device in accordance with claim 27 wherein said substrate is a plastic sheet of a polyester, a polycarbonate, or a polylmide; and said gate, source, and drain electrodes are each independently comprised of silver, gold, nickel, aluminum, chromium, platinum, or indium titanium oxide, or a conductive polymer, and said gate dielectric layer is comprised of inorganic nitrides or oxides, or organic polymers, silicon nitride, silicon oxide.

33. A device in accordance with claim 27 wherein the functionalized heteroacene comprises a mixture of the cis and trans isomers of said formula.

34. A thin film transistor comprised of a substrate, a gate electrode, a gate dielectric layer, a source electrode, a drain electrode and a layer containing at least one functionalized heteroacene selected from the group consisting of the formulas/structures:

(1)

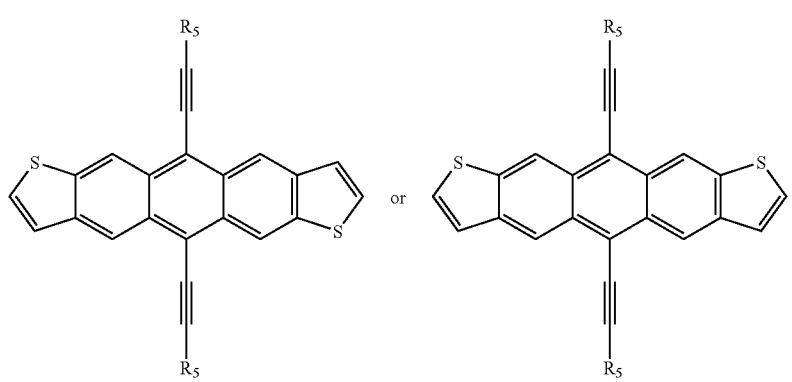

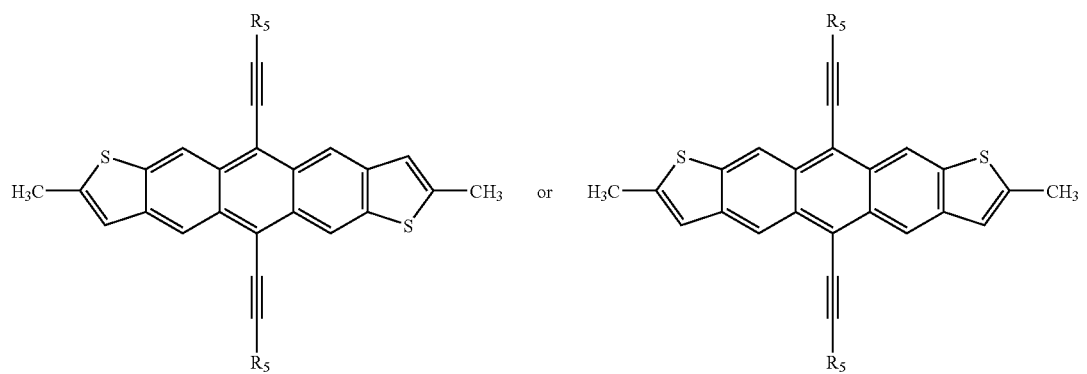
(2)
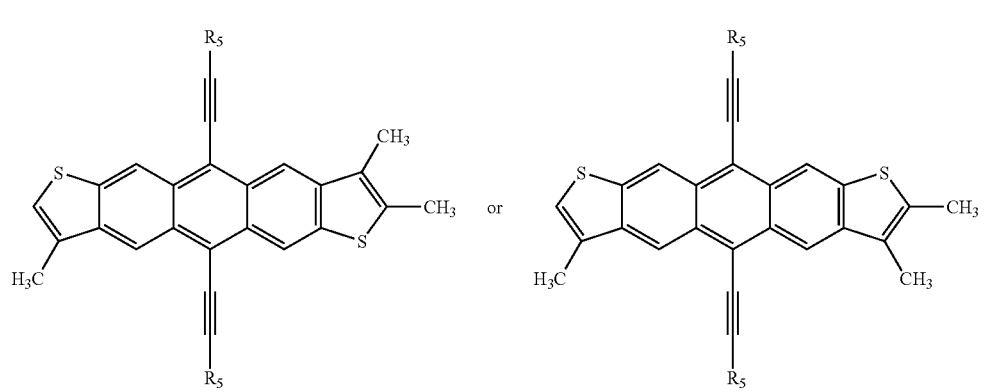
(3)
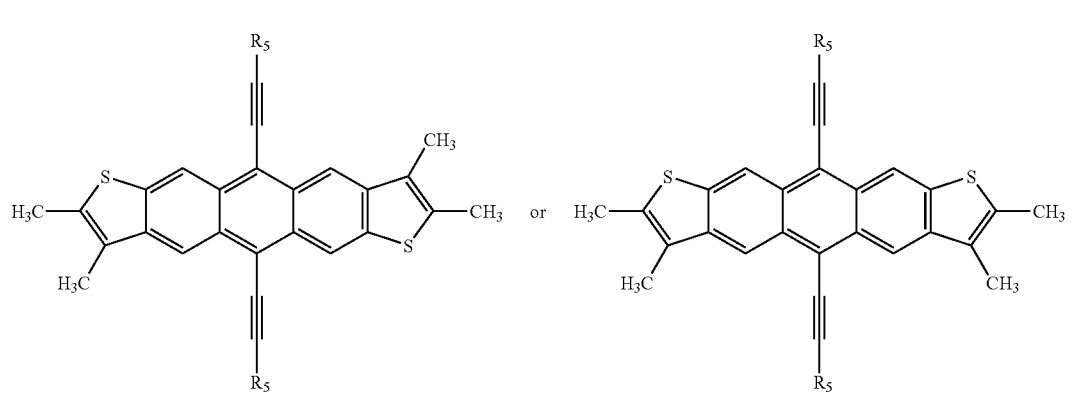
(4)
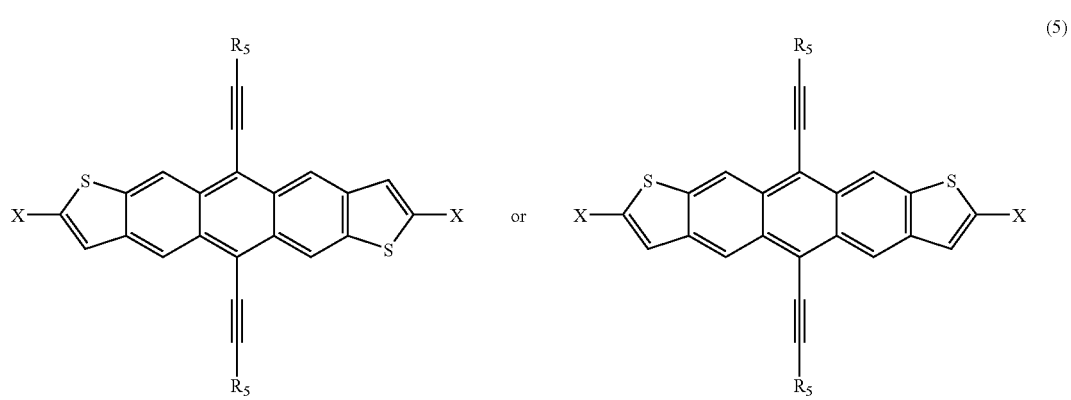
(5)

(6)
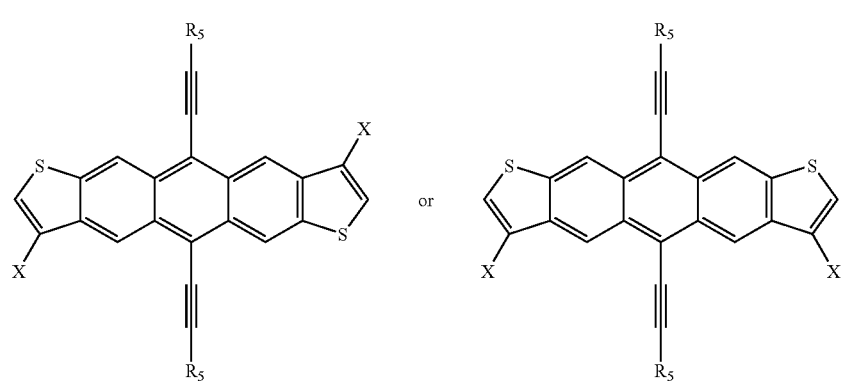
(7)
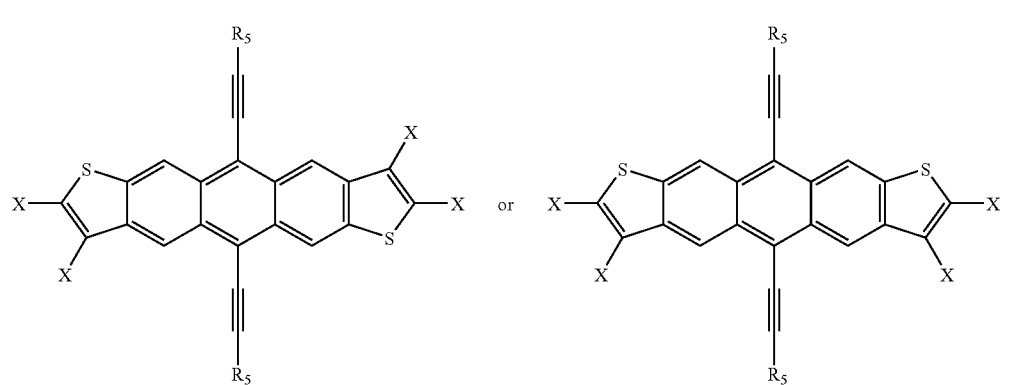
(8)
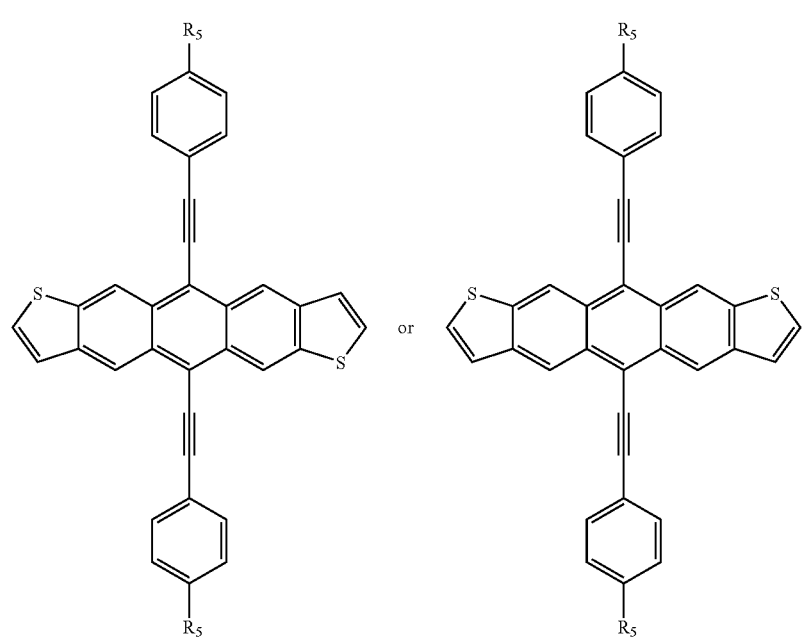

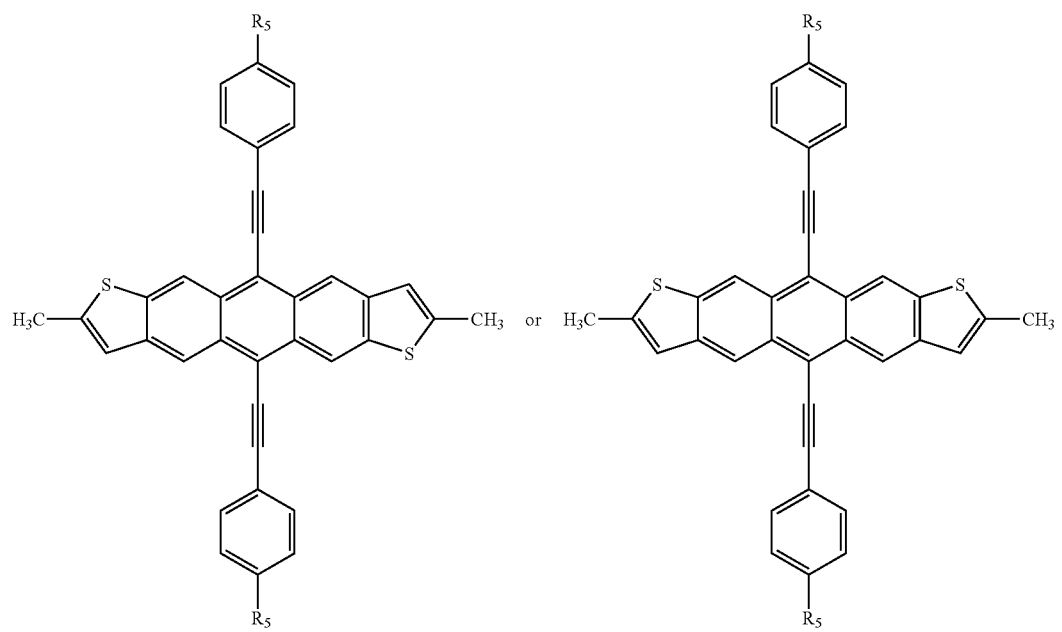
(9)
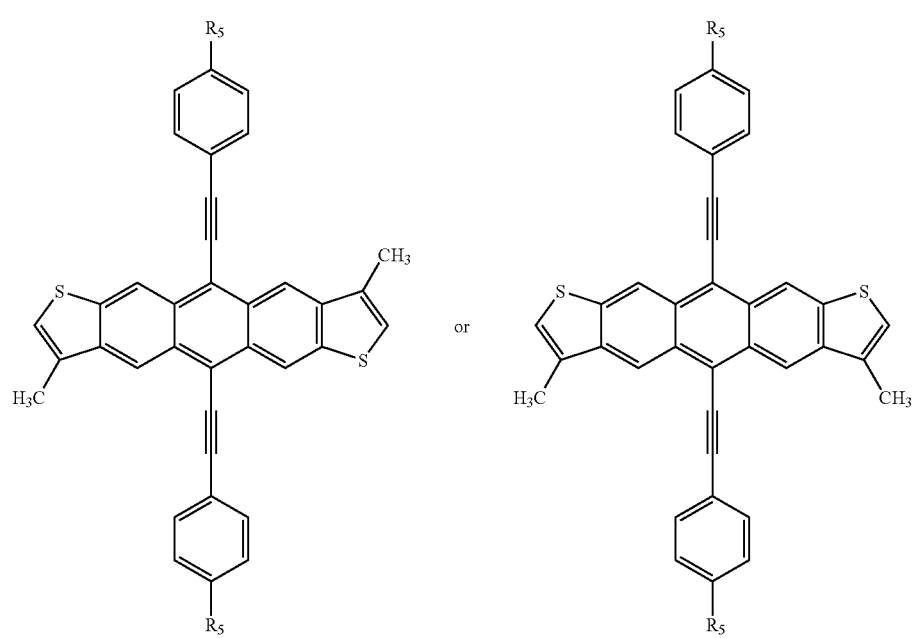
(10)

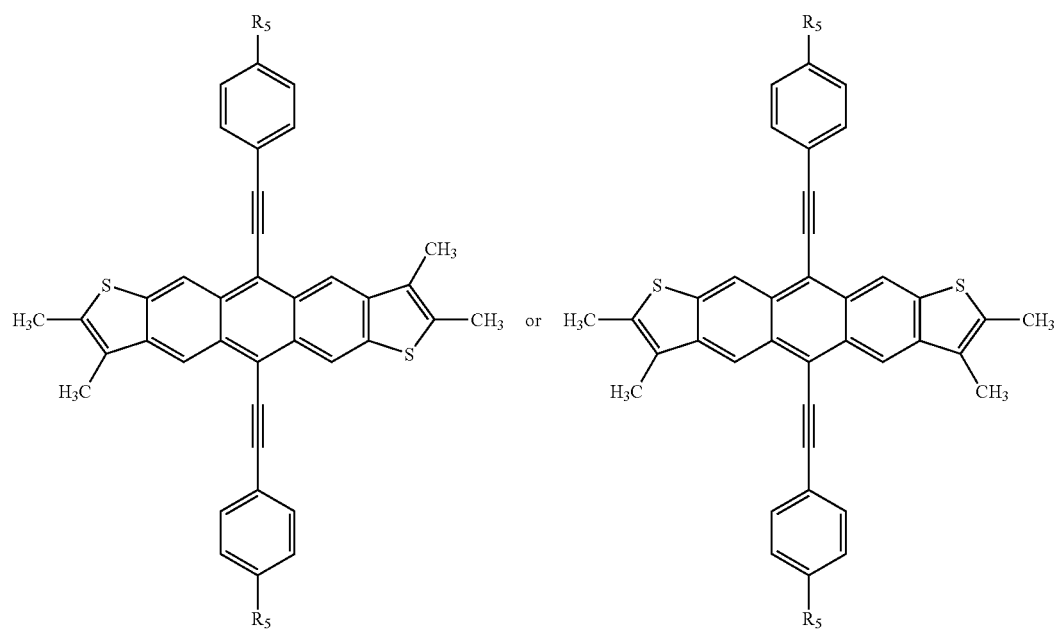
(11)
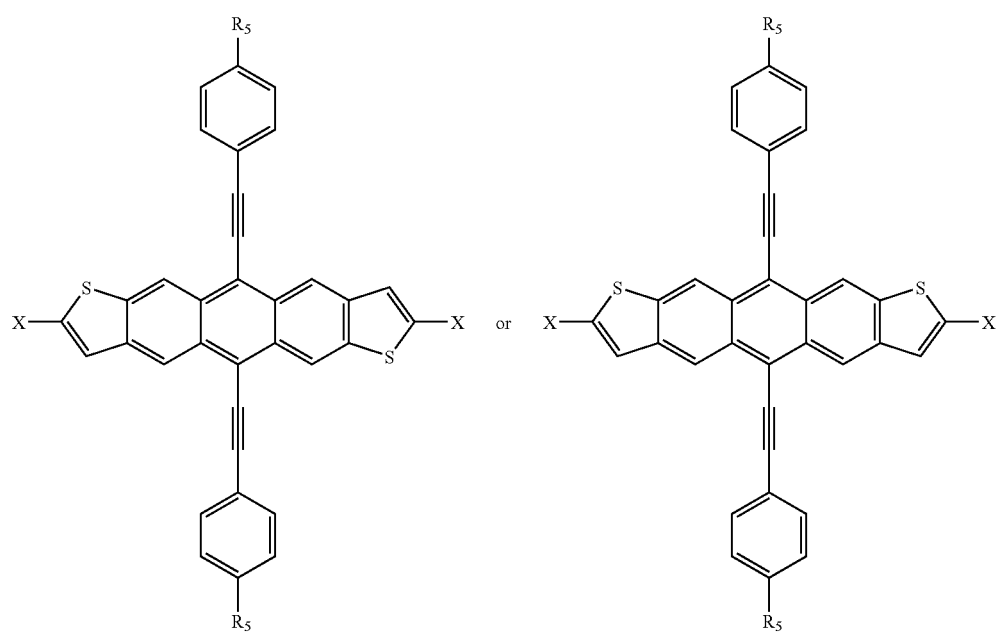
(12)

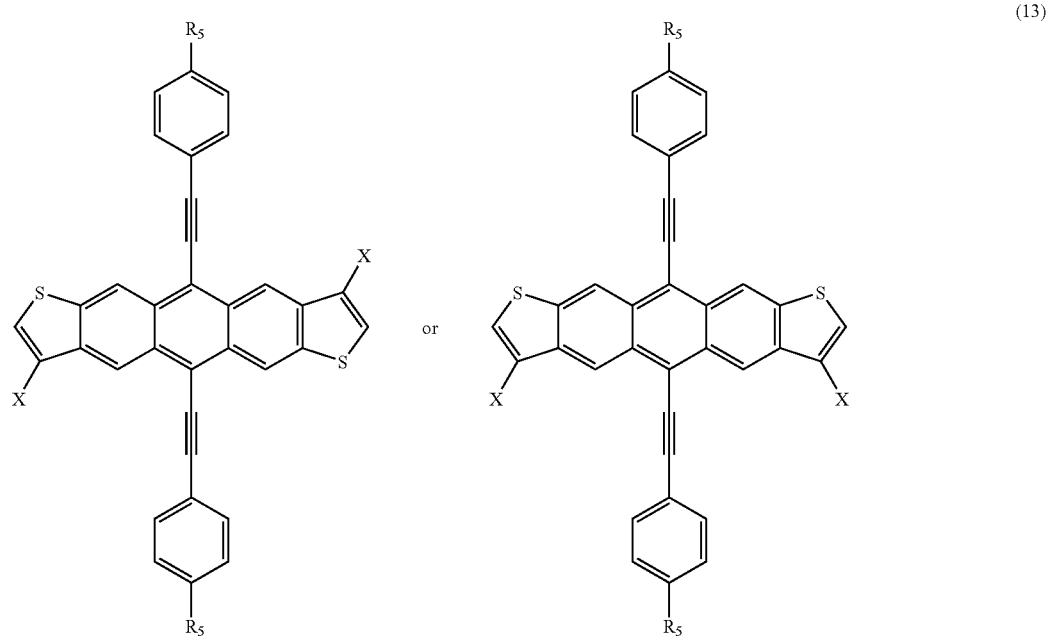
(13)
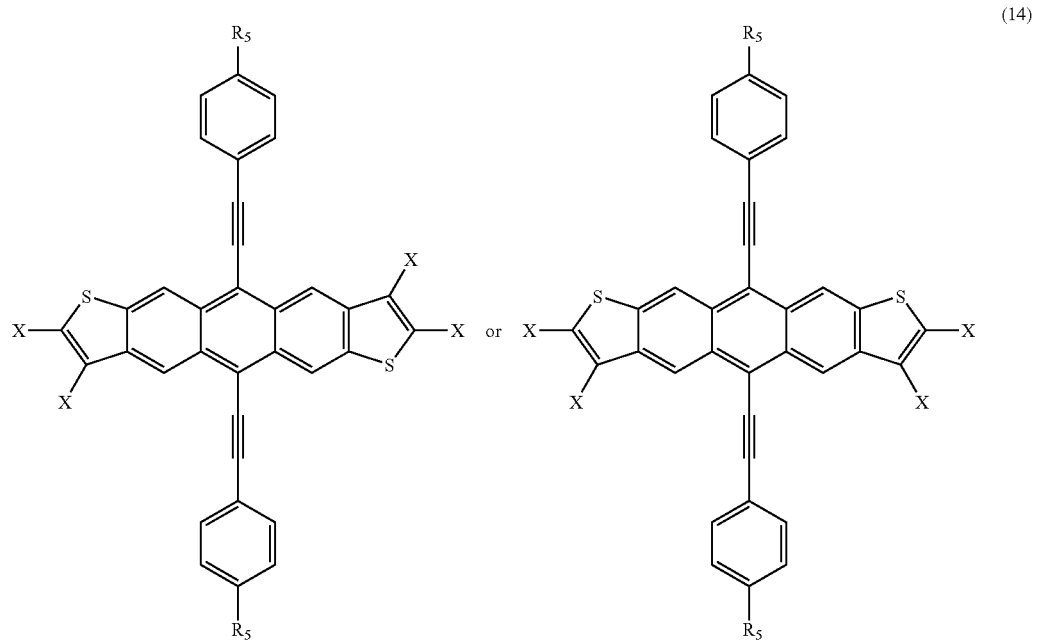
(14)

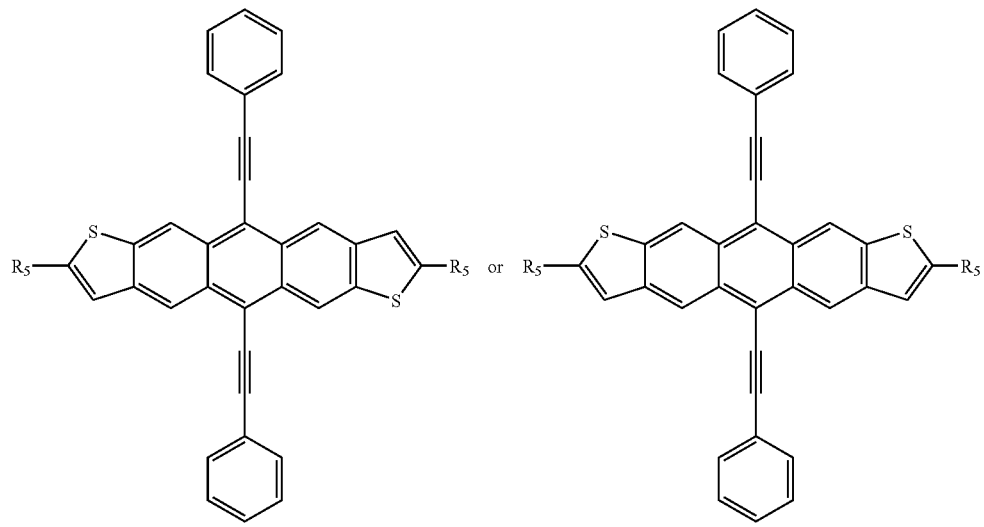
(15)
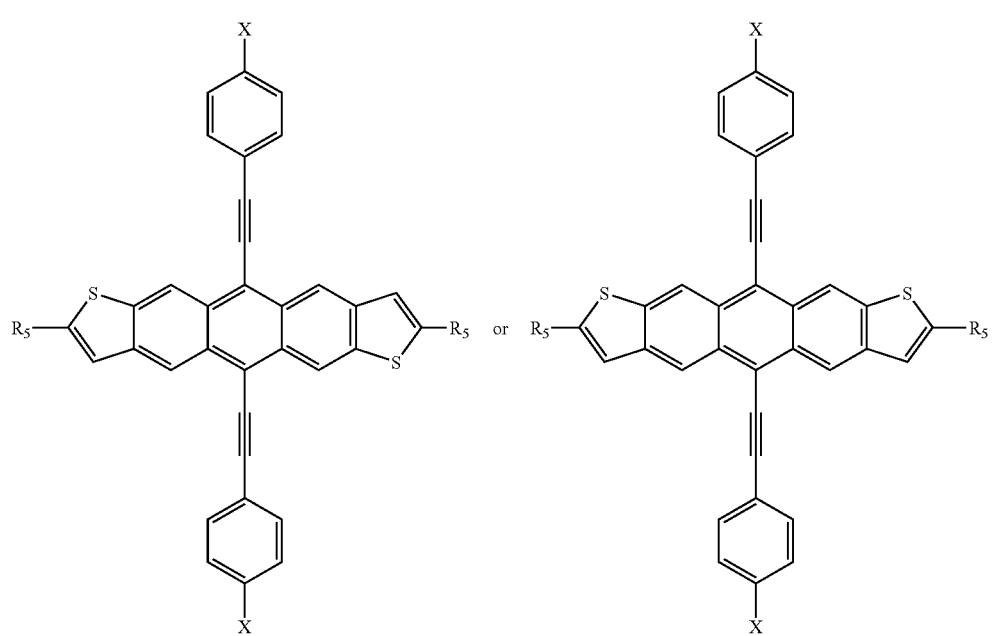
(16)

-continued
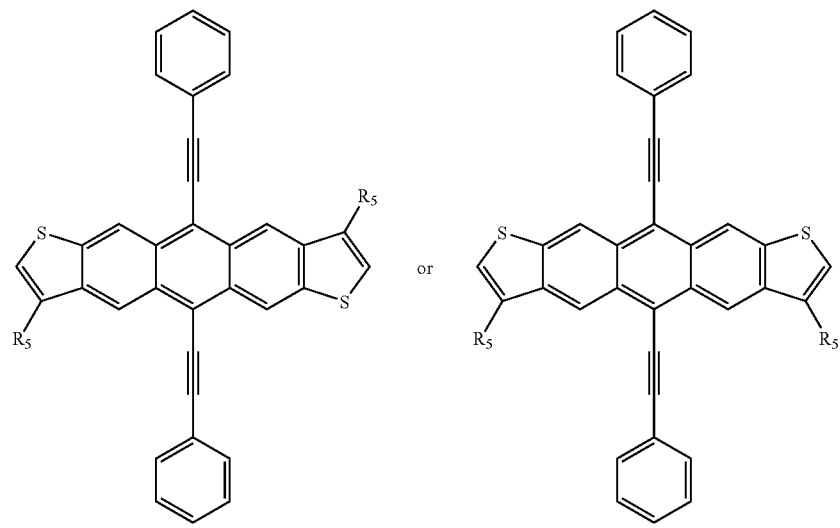
(17)
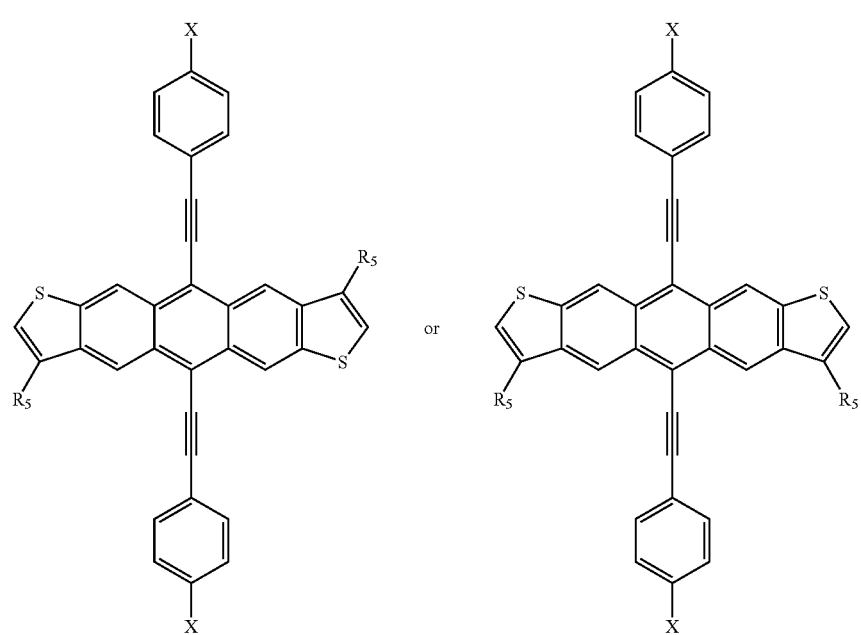
(18)

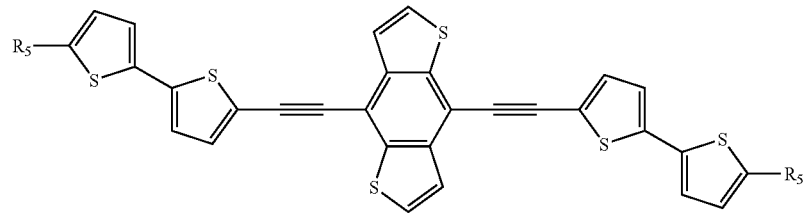
(19)
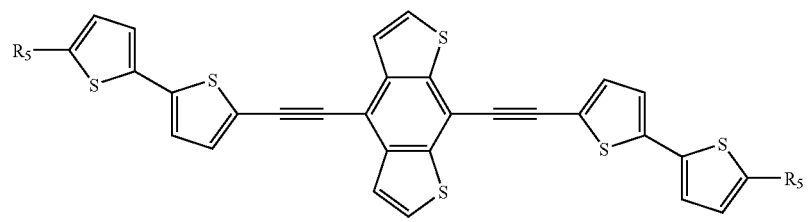
or
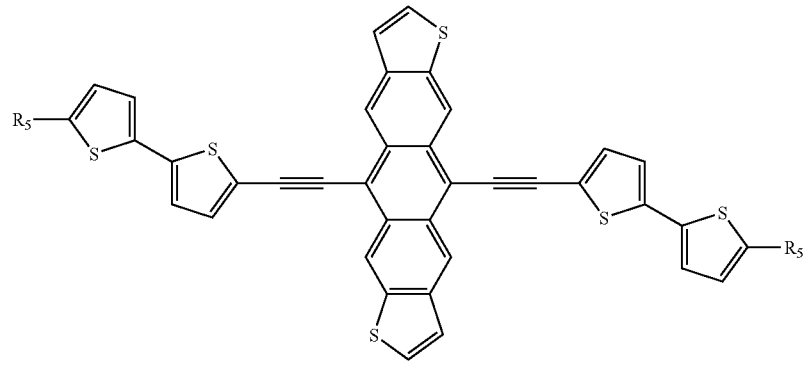
(20)
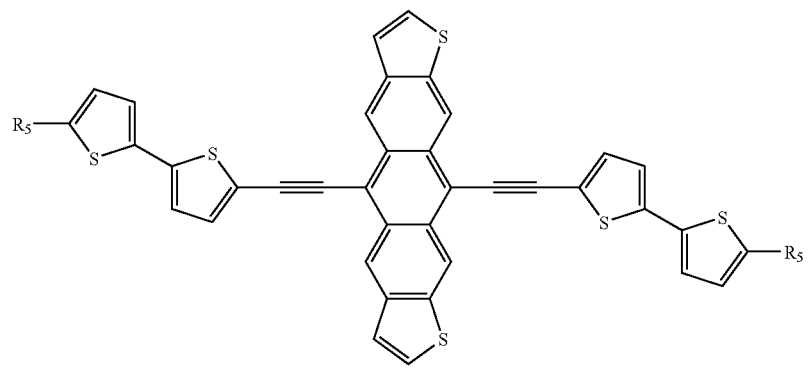
or

(21)
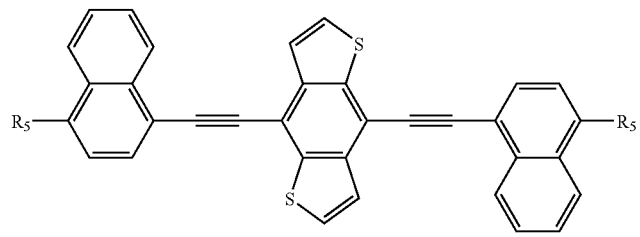
or
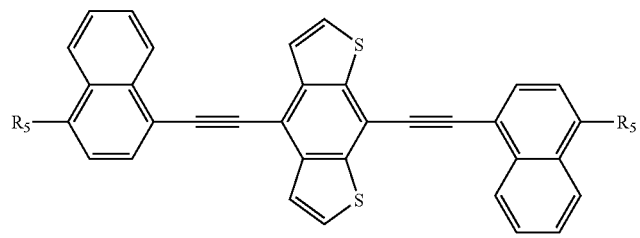
(22)
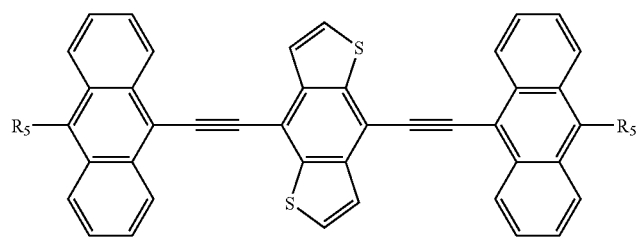
or
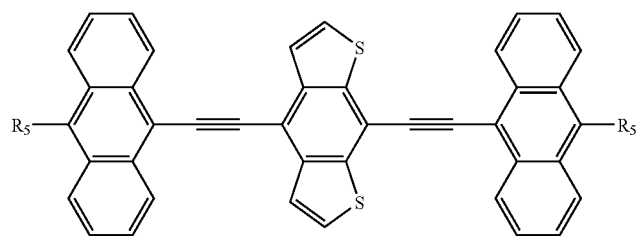

-continued
(23)
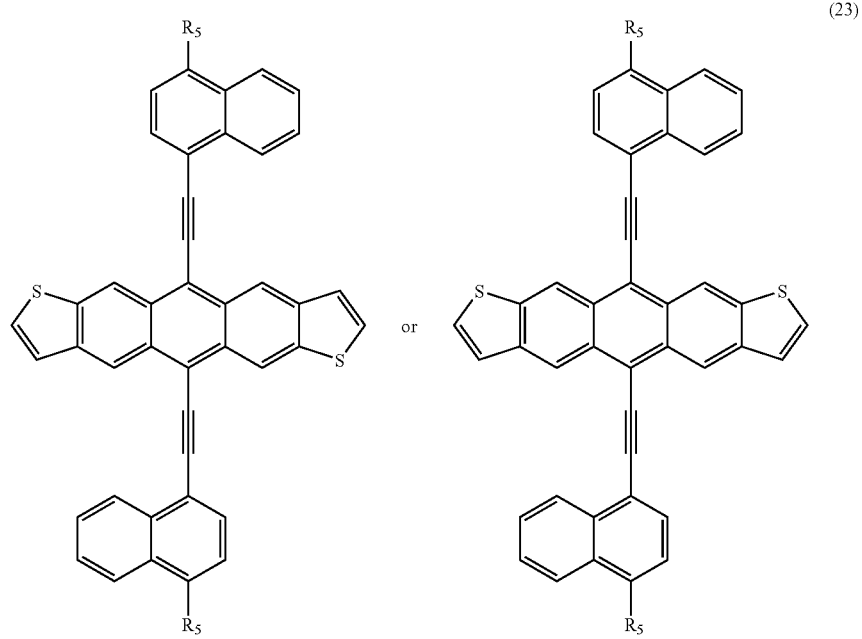
(24)
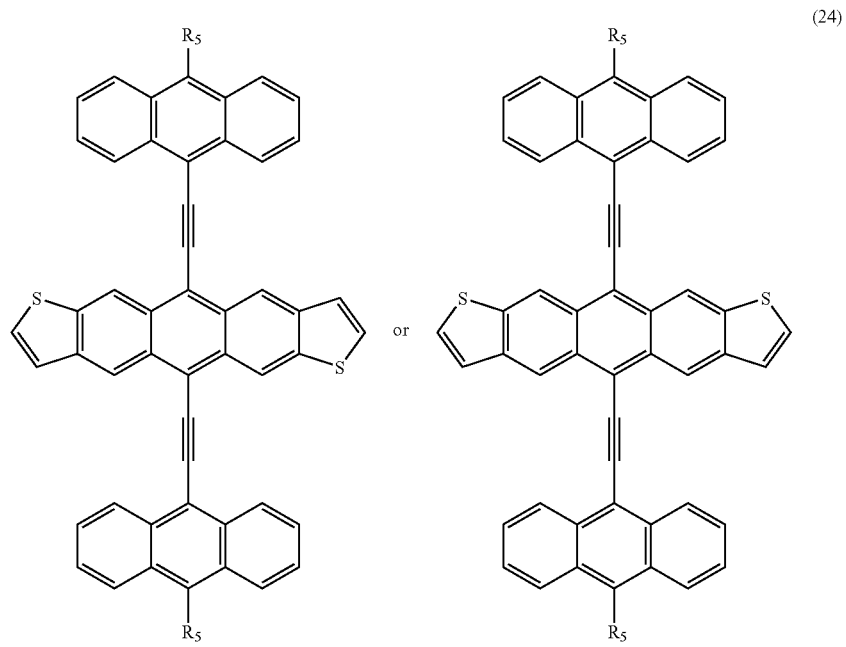

-continued
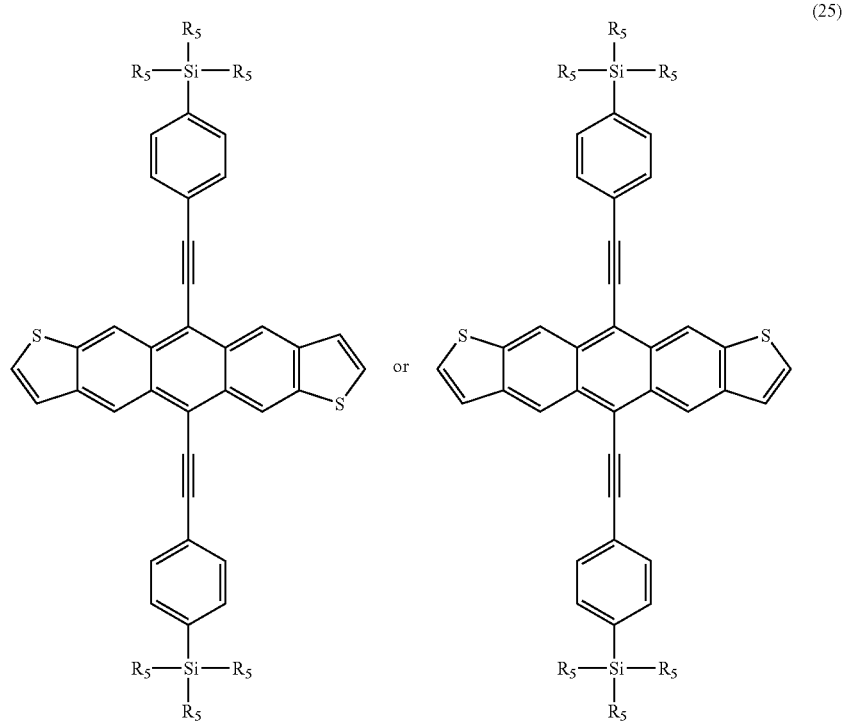
(25)
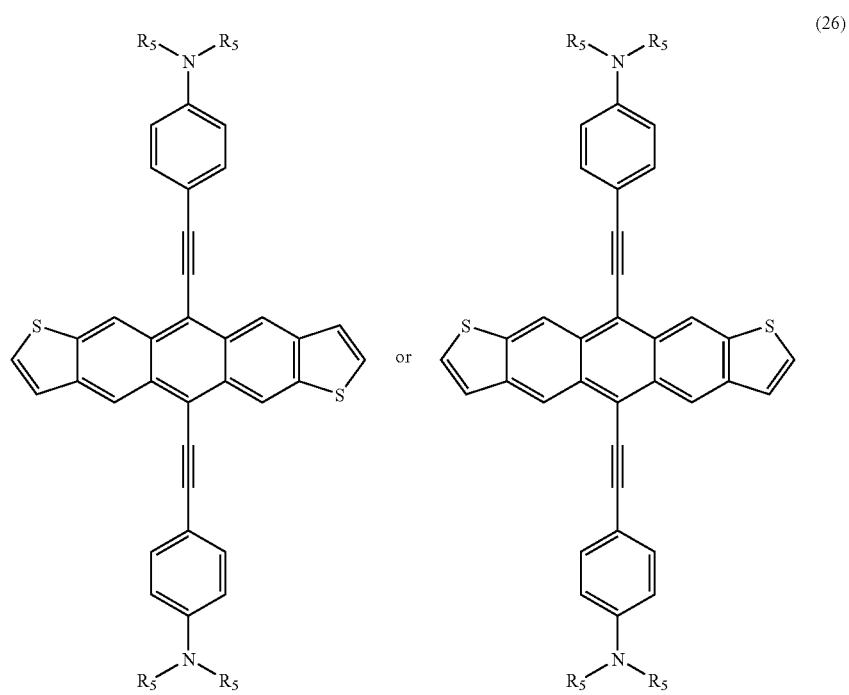
(26)

-continued

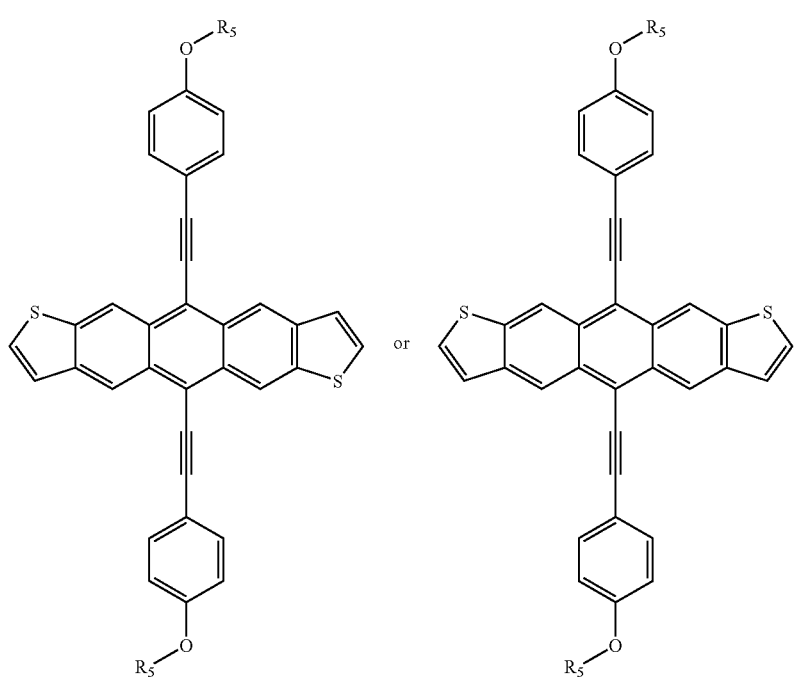

(27)

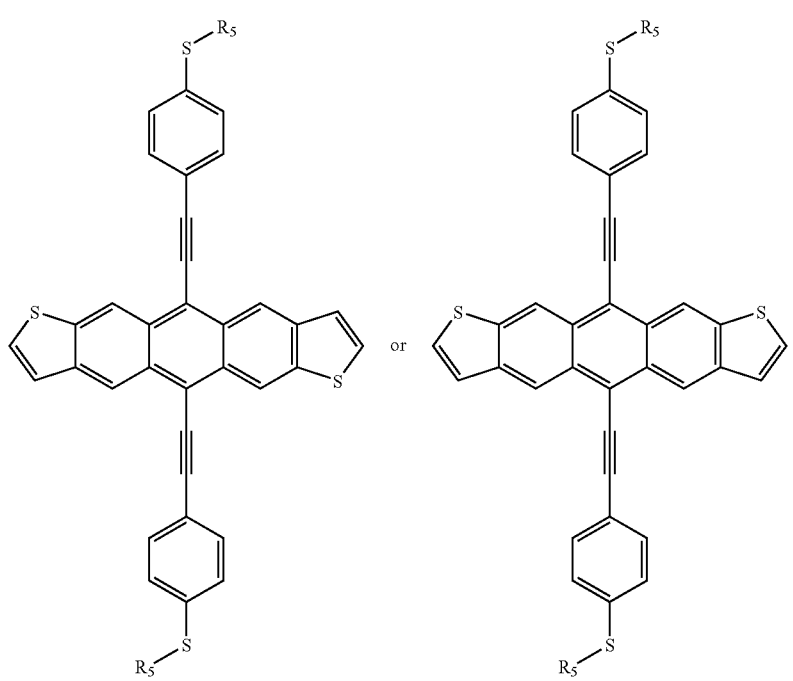

(28)

wherein $R_5$ is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, or octadecyl; trifluoromethyl, fluoroethyl, perfluoropropyl, perfluorobutyl, perfluoropentyl, perfluorohexyl, perfluoroheptyl, perfluorooctyl, perfluorononyl, perfluorodecyl, perfluoroundecyl, or perfluorododecyl; phenyl, methylphenyl (tolyl), ethylphenyl, propylphenyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, trifluoromethylphenyl, fluoroethylphenyl, perflucropropylphenyl, perfluorobutylphenyl, perfluoropentylphenyl, perfluorohexylphenyl, perfluoroheptylphenyl, perfluorooctylphenyl, perfluorononylphenyl, perfluorodecylphenyl, perfluoroundecylphenyl, or perflucrododecylphenyl; and wherein X is F, Cl, Br, CN, or $NO_2$.

* * * * *

UNITED STATES PATENT AND TRADEMARK OFFICE
CERTIFICATE OF CORRECTION

PATENT NO. : 7,372,071 B2
APPLICATION NO. : 11/398981
DATED : May 13, 2008
INVENTOR(S) : Yuning Li et al.

It is certified that error appears in the above-identified patent and that said Letters Patent is hereby corrected as shown below:

In the Specifications:

Column 1, line 10, after "Agreement No.", please delete "70NANBOH3033" and insert --70NANB0H3033--.

Signed and Sealed this
Third Day of September, 2013

Teresa Stanek Rea
*Acting Director of the United States Patent and Trademark Office*